US008423514B2

(12) United States Patent
Goldenberg et al.

(10) Patent No.: US 8,423,514 B2
(45) Date of Patent: Apr. 16, 2013

(54) SERVICE PROVISIONING

(75) Inventors: Glenn Goldenberg, Austin, TX (US); Jason Woods, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 328 days.

(21) Appl. No.: 11/967,735

(22) Filed: Dec. 31, 2007

(65) Prior Publication Data

US 2011/0010728 A1  Jan. 13, 2011

Related U.S. Application Data

(60) Provisional application No. 60/920,735, filed on Mar. 29, 2007.

(51) Int. Cl.
*G06F 17/30* (2006.01)
*G06F 9/46* (2006.01)

(52) U.S. Cl.
USPC ..................... 707/673; 719/329; 707/696

(58) Field of Classification Search ............... 707/999.1, 707/999.2, 999.001, 673, 696; 719/329
See application file for complete search history.

(56) References Cited

U.S. PATENT DOCUMENTS

| 4,531,186 A | 7/1985 | Knapman |
| 5,020,019 A | 5/1991 | Ogawa |
| 5,134,564 A | 7/1992 | Dunn et al. |
| 5,247,437 A | 9/1993 | Vale et al. |
| 5,321,833 A | 6/1994 | Chang et al. |
| 5,323,311 A | 6/1994 | Fukao et al. |
| 5,333,317 A | 7/1994 | Dann |
| 5,381,332 A | 1/1995 | Wood |
| 5,442,782 A | 8/1995 | Malatesta et al. |
| 5,497,486 A | 3/1996 | Stolfo et al. |
| 5,535,322 A | 7/1996 | Hecht |
| 5,535,382 A | 7/1996 | Ogawa |
| 5,537,590 A | 7/1996 | Amado |
| 5,555,409 A | 9/1996 | Leenstra et al. |

(Continued)

FOREIGN PATENT DOCUMENTS

| WO | 9855947 A1 | 12/1998 |
| WO | 0159586 | 8/2001 |

(Continued)

OTHER PUBLICATIONS

Fair, "Record Linkage in the National Dose Registry of Canada", European Journal of Cancer, vol. 3, Supp. 3, pp. S37-S43, XP005058648 ISSN: 0959-8049, Apr. 1997.

(Continued)

*Primary Examiner* — Pierre Vital
*Assistant Examiner* — Sabana Rahman
(74) *Attorney, Agent, or Firm* — Elissa Y. Wang; Edell, Shapiro & Finnan, LLC

(57) ABSTRACT

Embodiments disclosed herein provide systems and methods that can bridge the gap between business operations and data management operations. An interface layer provides customizable interfaces for interactions with a master entity index (MEI) system to accomplish association, storage, management or processing of data records based on user-defined business service operations. The interface layer allows a user to define business services, operations, and logical procedures according to a desired data model such that the inputs and outputs for each operation of the service correspond to the particular needs of the user and allow different terminology to be employed by the user.

16 Claims, 18 Drawing Sheets

U.S. PATENT DOCUMENTS

| | | | |
|---|---|---|---|
| 5,561,794 A | 10/1996 | Fortier | |
| 5,583,763 A | 12/1996 | Atcheson et al. | |
| 5,600,835 A | 2/1997 | Garland et al. | |
| 5,606,690 A | 2/1997 | Hunter et al. | |
| 5,615,367 A * | 3/1997 | Bennett et al. | 1/1 |
| 5,640,553 A | 6/1997 | Schultz | |
| 5,651,108 A | 7/1997 | Cain et al. | |
| 5,675,752 A | 10/1997 | Scott et al. | |
| 5,675,753 A | 10/1997 | Hansen et al. | |
| 5,694,593 A | 12/1997 | Baclawski | |
| 5,694,594 A | 12/1997 | Chang | |
| 5,710,916 A | 1/1998 | Barbara et al. | |
| 5,734,907 A | 3/1998 | Jarossay et al. | |
| 5,765,150 A | 6/1998 | Burrows | |
| 5,774,661 A | 6/1998 | Chatterjee | |
| 5,774,883 A | 6/1998 | Andersen | |
| 5,774,887 A | 6/1998 | Wolff et al. | |
| 5,778,370 A | 7/1998 | Emerson | |
| 5,787,431 A | 7/1998 | Shaughnessy | |
| 5,787,470 A | 7/1998 | DeSimone et al. | |
| 5,790,173 A | 8/1998 | Strauss | |
| 5,796,393 A | 8/1998 | MacNaughton et al. | |
| 5,805,702 A | 9/1998 | Curry | |
| 5,809,499 A | 9/1998 | Wong et al. | |
| 5,819,264 A | 10/1998 | Palmon et al. | |
| 5,835,712 A | 11/1998 | DuFresne | |
| 5,835,912 A | 11/1998 | Pet | |
| 5,848,271 A | 12/1998 | Caruso et al. | |
| 5,859,972 A | 1/1999 | Subramaniam et al. | |
| 5,862,322 A | 1/1999 | Anglin et al. | |
| 5,862,325 A | 1/1999 | Reed et al. | |
| 5,878,043 A | 3/1999 | Casey | |
| 5,893,074 A | 4/1999 | Hughes et al. | |
| 5,893,110 A | 4/1999 | Weber et al. | |
| 5,905,496 A | 5/1999 | Lau et al. | |
| 5,930,768 A | 7/1999 | Hooban | |
| 5,960,411 A | 9/1999 | Hartman et al. | |
| 5,963,915 A | 10/1999 | Kirsch | |
| 5,987,422 A | 11/1999 | Buzsaki | |
| 5,991,758 A * | 11/1999 | Ellard | 1/1 |
| 5,999,937 A | 12/1999 | Ellard | |
| 6,014,664 A | 1/2000 | Fagin et al. | |
| 6,016,489 A | 1/2000 | Cavanaugh et al. | |
| 6,018,733 A | 1/2000 | Kirsch et al. | |
| 6,018,742 A | 1/2000 | Herbert, III | |
| 6,026,433 A | 2/2000 | D'Arlach et al. | |
| 6,049,847 A | 4/2000 | Vogt et al. | |
| 6,067,549 A | 5/2000 | Smalley et al. | |
| 6,069,628 A | 5/2000 | Farry et al. | |
| 6,078,325 A | 6/2000 | Jolissaint et al. | |
| 6,108,004 A | 8/2000 | Medl | |
| 6,134,581 A | 10/2000 | Ismael et al. | |
| 6,185,608 B1 | 2/2001 | Hon et al. | |
| 6,223,145 B1 | 4/2001 | Hearst | |
| 6,269,373 B1 | 7/2001 | Apte et al. | |
| 6,297,824 B1 | 10/2001 | Hearst et al. | |
| 6,298,478 B1 | 10/2001 | Nally et al. | |
| 6,311,190 B1 | 10/2001 | Bayer et al. | |
| 6,327,611 B1 | 12/2001 | Everingham | |
| 6,330,569 B1 | 12/2001 | Baisley et al. | |
| 6,356,931 B2 | 3/2002 | Ismael et al. | |
| 6,374,241 B1 | 4/2002 | Lamburt et al. | |
| 6,385,600 B1 | 5/2002 | McGuinness et al. | |
| 6,389,429 B1 | 5/2002 | Kane et al. | |
| 6,446,188 B1 | 9/2002 | Henderson et al. | |
| 6,449,620 B1 | 9/2002 | Draper | |
| 6,457,065 B1 | 9/2002 | Rich et al. | |
| 6,460,045 B1 | 10/2002 | Aboulnaga et al. | |
| 6,496,793 B1 | 12/2002 | Veditz et al. | |
| 6,502,099 B1 | 12/2002 | Rampy et al. | |
| 6,510,505 B1 | 1/2003 | Burns et al. | |
| 6,523,019 B1 | 2/2003 | Borthwick | |
| 6,529,888 B1 | 3/2003 | Heckerman et al. | |
| 6,556,983 B1 | 4/2003 | Altschuler et al. | |
| 6,557,100 B1 | 4/2003 | Knutson | |
| 6,621,505 B1 | 9/2003 | Beauchamp et al. | |
| 6,633,878 B1 | 10/2003 | Underwood | |
| 6,633,882 B1 | 10/2003 | Fayyad et al. | |
| 6,633,992 B1 | 10/2003 | Rosen | |
| 6,647,383 B1 | 11/2003 | August et al. | |
| 6,662,180 B1 | 12/2003 | Aref et al. | |
| 6,687,702 B2 | 2/2004 | Vaitheeswaran et al. | |
| 6,704,805 B1 | 3/2004 | Acker et al. | |
| 6,718,535 B1 | 4/2004 | Underwood | |
| 6,742,003 B2 | 5/2004 | Heckerman et al. | |
| 6,757,708 B1 | 6/2004 | Craig et al. | |
| 6,795,793 B2 | 9/2004 | Shayegan et al. | |
| 6,807,537 B1 | 10/2004 | Thiesson et al. | |
| 6,842,761 B2 | 1/2005 | Diamond et al. | |
| 6,842,906 B1 | 1/2005 | Bowman-Amuah | |
| 6,879,944 B1 | 4/2005 | Tipping et al. | |
| 6,907,422 B1 | 6/2005 | Predovic | |
| 6,912,549 B2 | 6/2005 | Rotter et al. | |
| 6,922,695 B2 | 7/2005 | Skufca et al. | |
| 6,957,186 B1 | 10/2005 | Guheen et al. | |
| 6,990,636 B2 | 1/2006 | Beauchamp et al. | |
| 6,996,565 B2 | 2/2006 | Skufca et al. | |
| 7,035,809 B2 | 4/2006 | Miller et al. | |
| 7,043,476 B2 | 5/2006 | Robson | |
| 7,099,857 B2 | 8/2006 | Lambert | |
| 7,143,091 B2 | 11/2006 | Charnock et al. | |
| 7,155,427 B1 | 12/2006 | Prothia | |
| 7,181,459 B2 | 2/2007 | Grant et al. | |
| 7,249,131 B2 | 7/2007 | Skufca et al. | |
| 7,330,845 B2 | 2/2008 | Lee et al. | |
| 7,487,173 B2 | 2/2009 | Medicke et al. | |
| 7,526,486 B2 | 4/2009 | Cushman, II et al. | |
| 7,567,962 B2 | 7/2009 | Chakrabarti et al. | |
| 7,620,647 B2 | 11/2009 | Stephens et al. | |
| 7,627,550 B1 | 12/2009 | Adams et al. | |
| 7,685,093 B1 | 3/2010 | Adams et al. | |
| 7,698,268 B1 | 4/2010 | Adams et al. | |
| 7,788,274 B1 | 8/2010 | Ionescu | |
| 8,321,383 B2 | 11/2012 | Schumacher et al. | |
| 8,321,393 B2 | 11/2012 | Adams et al. | |
| 8,332,366 B2 | 12/2012 | Schumacher et al. | |
| 2002/0007284 A1 | 1/2002 | Schurenberg et al. | |
| 2002/0073099 A1 | 6/2002 | Gilbert et al. | |
| 2002/0080187 A1 | 6/2002 | Lawton | |
| 2002/0087599 A1 | 7/2002 | Grant et al. | |
| 2002/0095421 A1 | 7/2002 | Koskas | |
| 2002/0099694 A1 | 7/2002 | Diamond et al. | |
| 2002/0152422 A1 | 10/2002 | Sharma et al. | |
| 2002/0156917 A1 | 10/2002 | Nye | |
| 2002/0178360 A1 | 11/2002 | Wenocur et al. | |
| 2003/0004770 A1 | 1/2003 | Miller et al. | |
| 2003/0004771 A1 | 1/2003 | Yaung | |
| 2003/0018652 A1 | 1/2003 | Heckerman et al. | |
| 2003/0023773 A1 * | 1/2003 | Lee et al. | 709/328 |
| 2003/0051063 A1 | 3/2003 | Skufca et al. | |
| 2003/0065826 A1 | 4/2003 | Skufca et al. | |
| 2003/0065827 A1 | 4/2003 | Skufca et al. | |
| 2003/0105825 A1 | 6/2003 | Kring et al. | |
| 2003/0120630 A1 | 6/2003 | Tunkelang | |
| 2003/0145002 A1 | 7/2003 | Kleinberger et al. | |
| 2003/0158850 A1 | 8/2003 | Lawrence et al. | |
| 2003/0174179 A1 | 9/2003 | Suermondt et al. | |
| 2003/0182101 A1 | 9/2003 | Lambert | |
| 2003/0195836 A1 | 10/2003 | Hayes et al. | |
| 2003/0195889 A1 | 10/2003 | Yao et al. | |
| 2003/0195890 A1 | 10/2003 | Oommen | |
| 2003/0220858 A1 | 11/2003 | Lam et al. | |
| 2003/0227487 A1 | 12/2003 | Hugh | |
| 2004/0107189 A1 | 6/2004 | Burdick et al. | |
| 2004/0107205 A1 | 6/2004 | Burdick et al. | |
| 2004/0122790 A1 | 6/2004 | Walker et al. | |
| 2004/0143477 A1 | 7/2004 | Wolff | |
| 2004/0143508 A1 | 7/2004 | Bohn et al. | |
| 2004/0181526 A1 | 9/2004 | Burdick et al. | |
| 2004/0181554 A1 | 9/2004 | Heckerman et al. | |
| 2004/0220926 A1 | 11/2004 | Lamkin et al. | |
| 2004/0260694 A1 | 12/2004 | Chaudhuri et al. | |
| 2005/0004895 A1 | 1/2005 | Schurenberg et al. | |
| 2005/0015381 A1 | 1/2005 | Clifford et al. | |
| 2005/0015675 A1 | 1/2005 | Kolawa et al. | |
| 2005/0050068 A1 | 3/2005 | Vaschillo et al. | |
| 2005/0055345 A1 | 3/2005 | Ripley | |

| | | |
|---|---|---|
| 2005/0060286 A1 | 3/2005 | Hansen et al. |
| 2005/0071194 A1 | 3/2005 | Bormann et al. |
| 2005/0075917 A1 | 4/2005 | Flores et al. |
| 2005/0114369 A1 | 5/2005 | Gould et al. |
| 2005/0149522 A1 | 7/2005 | Cookson et al. |
| 2005/0154615 A1 | 7/2005 | Rotter et al. |
| 2005/0210007 A1 | 9/2005 | Beres et al. |
| 2005/0228808 A1 | 10/2005 | Mamou et al. |
| 2005/0240392 A1 | 10/2005 | Munro et al. |
| 2005/0256740 A1 | 11/2005 | Kohan et al. |
| 2005/0256882 A1* | 11/2005 | Able et al. ............... 707/10 |
| 2005/0273452 A1 | 12/2005 | Molloy et al. |
| 2006/0053151 A1 | 3/2006 | Gardner et al. |
| 2006/0053172 A1 | 3/2006 | Gardner et al. |
| 2006/0053173 A1 | 3/2006 | Gardner et al. |
| 2006/0053382 A1 | 3/2006 | Gardner et al. |
| 2006/0064429 A1 | 3/2006 | Yao |
| 2006/0074832 A1 | 4/2006 | Gardner et al. |
| 2006/0074836 A1 | 4/2006 | Gardner et al. |
| 2006/0080312 A1 | 4/2006 | Friedlander et al. |
| 2006/0116983 A1 | 6/2006 | Dettinger et al. |
| 2006/0117032 A1 | 6/2006 | Dettinger et al. |
| 2006/0129605 A1 | 6/2006 | Doshi |
| 2006/0129971 A1 | 6/2006 | Rojer |
| 2006/0136205 A1 | 6/2006 | Song |
| 2006/0161522 A1 | 7/2006 | Dettinger et al. |
| 2006/0167896 A1 | 7/2006 | Kapur et al. |
| 2006/0179050 A1 | 8/2006 | Giang et al. |
| 2006/0190445 A1 | 8/2006 | Risberg et al. |
| 2006/0195560 A1 | 8/2006 | Newport |
| 2006/0265400 A1 | 11/2006 | Fain et al. |
| 2006/0271401 A1* | 11/2006 | Lassetter et al. ............... 705/2 |
| 2006/0271549 A1 | 11/2006 | Rayback et al. |
| 2006/0287890 A1 | 12/2006 | Stead et al. |
| 2007/0005567 A1 | 1/2007 | Hermansen et al. |
| 2007/0016450 A1 | 1/2007 | Bhora et al. |
| 2007/0055647 A1 | 3/2007 | Mullins et al. |
| 2007/0067285 A1 | 3/2007 | Blume et al. |
| 2007/0073678 A1 | 3/2007 | Scott et al. |
| 2007/0073745 A1 | 3/2007 | Scott et al. |
| 2007/0094060 A1 | 4/2007 | Apps et al. |
| 2007/0150279 A1 | 6/2007 | Gandhi et al. |
| 2007/0192715 A1 | 8/2007 | Kataria et al. |
| 2007/0198481 A1 | 8/2007 | Hogue et al. |
| 2007/0198600 A1 | 8/2007 | Betz |
| 2007/0214129 A1 | 9/2007 | Ture et al. |
| 2007/0214179 A1 | 9/2007 | Hoang |
| 2007/0217676 A1 | 9/2007 | Grauman et al. |
| 2007/0250487 A1 | 10/2007 | Reuther |
| 2007/0260492 A1* | 11/2007 | Feied et al. ............... 705/3 |
| 2007/0276844 A1 | 11/2007 | Segal et al. |
| 2007/0276858 A1 | 11/2007 | Cushman et al. |
| 2007/0299697 A1 | 12/2007 | Friedlander et al. |
| 2007/0299842 A1 | 12/2007 | Morris et al. |
| 2008/0005106 A1 | 1/2008 | Schumacher et al. |
| 2008/0016218 A1 | 1/2008 | Jones et al. |
| 2008/0069132 A1 | 3/2008 | Ellard et al. |
| 2008/0120432 A1 | 5/2008 | Lamoureux et al. |
| 2008/0126160 A1 | 5/2008 | Takuechi et al. |
| 2008/0243832 A1 | 10/2008 | Adams et al. |
| 2008/0243885 A1 | 10/2008 | Harger et al. |
| 2008/0244008 A1 | 10/2008 | Wilkinson et al. |
| 2009/0089317 A1 | 4/2009 | Ford et al. |
| 2009/0089332 A1 | 4/2009 | Harger et al. |
| 2009/0089630 A1 | 4/2009 | Goldenberg et al. |
| 2009/0198686 A1 | 8/2009 | Cushman, II et al. |
| 2010/0114877 A1 | 5/2010 | Adams et al. |
| 2010/0174725 A1 | 7/2010 | Adams et al. |
| 2010/0175024 A1 | 7/2010 | Schumacher et al. |
| 2011/0010214 A1 | 1/2011 | Carruth |
| 2011/0010346 A1 | 1/2011 | Goldenberg et al. |
| 2011/0010401 A1 | 1/2011 | Adams et al. |
| 2011/0010728 A1 | 1/2011 | Goldenberg et al. |
| 2011/0047044 A1 | 2/2011 | Wright et al. |
| 2011/0191349 A1 | 8/2011 | Ford et al. |

FOREIGN PATENT DOCUMENTS

| | | |
|---|---|---|
| WO | 0159586 A2 | 8/2001 |
| WO | 0175679 A1 | 10/2001 |
| WO | 03021485 | 3/2003 |
| WO | 2004023297 A1 | 3/2004 |
| WO | 2004023311 A1 | 3/2004 |
| WO | 2004023345 A1 | 3/2004 |
| WO | 2009042931 A1 | 4/2009 |
| WO | 2009042941 A1 | 4/2009 |

OTHER PUBLICATIONS

International Search Report and Written Opinion, for PCT/US2007/012073, Mailed Jul. 23, 2008, 12 pages.
International Preliminary Report on Patentability Issued in PCT/US2007/013049, Mailed Dec. 17, 2008.
International Search Report and Written Opinion issued in PCT/US2007/013049, mailed Jun. 13, 2008.
Office Action issued in U.S. Appl. No. 11/809,792, mailed Aug. 21, 2009, 14 pages.
Oracle Data Hubs: "The Emperor Has No Clothes?", Feb. 21, 2005, Google.com, pp. 1-9.
IEEE, no matched results, Jun. 30, 2009, p. 1.
IEEE, no matched results, 1 pg., Sep. 11, 2009.
Office Action issued in U.S. Appl. No. 11/522,223 dated Aug. 20, 2008, 16 pgs.
Office Action issued in U.S. Appl. No. 11/522,223 dated Feb. 5, 2009, Adams, 17 pages.
Notice of Allowance issued for U.S. Appl. No. 11/522,223, dated Sep. 17, 2009, 20 pages.
De Rose, et al. "Building Structured Web Community Portals: A Top-Down, Compositional, and Incremental Approach", VDLB, ACM, pp. 399-410, Sep. 2007.
Microsoft Dictionary, "normalize", at p. 20, Fifth Edition, Microsoft Corp., downloaded from http://proquest.safaribooksonline.com/0735614954 on Sep. 8, 2008.
Office Action issued in U.S. Appl. No. 11/521,928 dated Apr. 1, 2009, 22 pages.
Office Action issued in U.S. Appl. No. 11/521,928 dated Sep. 16, 2008, 14 pages.
Notice of Allowance issued for U.S. Appl. No. 11/521,928, dated Sep. 18, 2009, 20 pages.
Gopalan Suresh Raj, Modeling Using Session and Entity Beans, Dec. 1998, Web Cornucopia, pp. 1-15.
Scott W. Ambler, Overcoming Data Design Challenges, Aug. 2001, p. 1-3.
XML, Java, and the future of the Web, Bosak, J., Sun Microsystems, Mar. 10, 1997, pp. 1-9.
Integrated Document and Workflow Management applied to Offer Processing a Machine Tool Company, Stefan Morschheuser, et al., Dept. of Information Systems I, COOCS '95 Milpitas CA, ACM 0-89791-706-5/95, p. 106-115.
Hamming Distance, HTML. Wikipedia.org, Available: http://en.wikipedia.org/wiki/Hamming_distance (as of May 8, 2008).
Office Action Issued in U.S. Appl. No. 11/521,946 mailed May 14, 2008, 10 pgs.
Office Action issued in U.S. Appl. No. 11/521,946 mailed Dec. 9, 2008, 10 pgs.
Office Action issued in U.S. Appl. No. 11/521,946 mailed May 13, 2009, 12 pgs.
Freund et al., Statistical Methods, 1993, Academic Press Inc., United Kingdom Edition, pp. 112-117.
Merriam-Webster dictionary defines "member" as "individuals".
Waddington, D., "Does it signal convergence of operational and analytic MDM?" retrieved from the internet:<URL: http://www.intelligententerprise.com>, 2 pages, Aug. 2006.
International Search Report mailed on Oct. 10, 2008, for PCT Application No. PCT/US07/20311 (10 pp).
International Search Report and Written Opinion issued in PCT/US07/89211, mailing date of Jun. 20, 2008.
International Search Report and Written Opinion for PCT/US08/58404, dated Aug. 15, 2008.
International Preliminary Report on Patentability Under Chapter 1 for PCT Application No. PCT/US2008/058665, issued Sep. 29, 2009, mailed Oct. 8, 2009, 6 pgs.
International Search Report and Written Opinion mailed on Dec. 3, 2008 for International Patent Application No. PCT/US2008/077985.

Gu, Lifang, et al., "Record Linkage: Current Practice and Future Directions," CSIRO Mathematical and Informational Sciences, 2003, pp. 1-32.

O'Hara-Schettino, et al., "Dynamic Navigation in Multiple View Software Specifications and Designs," Journal of Systems and Software, vol. 41, Issue 2, May 1998, pp. 93-103.

International Search Report and Written Opinion mailed on Oct. 10, 2008 for PCT Application No. PCT/US08/68979.

International Search Report and Written Opinion mailed on Dec. 2, 2008 for PCT/US2008/077970.

Martha E. Fair, et al., "Tutorial on Record Linkage Slides Presentation", Chapter 12, pp. 457-479.

International Search Report and Written Opinion mailed on Aug. 28, 2008 for Application No. PCT/US2008/58665, 7 pgs.

C.C. Gotlieb, Oral Interviews with C.C. Gotlieb, Apr. 1992, May 1992, ACM, pp. 1-72.

Google.com, no match results, Jun. 30, 2009, p. 1.

Supplementary European Search Report for EP 07 79 5659 dated May 18, 2010, 5 pages.

European Communication for EP 98928878 (PCT/US9811438) dated Feb. 16, 2006.

European Communication for EP 98928878 (PCT/US9811438) dated Mar. 10, 2008.

European Communication for EP 98928878 (PCT/US9811438) dated Jun. 26, 2006.

Gill, "Ox-Link: The Oxford Medical Record Linkage System", Internet Citation, 1997.

Newcombe et al., "The Use of Names for Linking Personal Records", Journal of the American Statistical Association, vol. 87, Dec. 1, 1992, pp. 335-349.

Jason Woods, et al. "Baja Identity Hub Configuration Process", Publicly available on Apr. 2, 2009, Version 1.3.

Initiate Systems, Inc. "Refining the Auto-Link Threshold Based Upon Scored Sample", Publicly available on Apr. 2, 2009; memorandum.

Initiate Systems, Inc. "Introduction", "False-Positive Rate (Auto-Link Threshold)", Publicly available on Apr. 2, 2009; memorandum.

Jason Woods, "Workbench 8.0 Bucket Analysis Tools", Publicly available on Apr. 2, 2009.

"Parsing" Publicly available on Oct. 2, 2008.

Initiate, "Business Scenario: Multi-Lingual Algorithm and Hub," Publicly available on Apr. 2, 2009.

Initiate, "Business Scenario: Multi-Lingual & Many-To-Many Entity Solutions", Publicly available on Apr. 2, 2009.

Initiate, "Relationships-MLH", presentation; Publicly available on Sep. 28, 2007.

Initiate, "Multi-Lingual Hub Support via Memtype Expansion", Publicly available on Apr. 2, 2009.

Initiate Systems, Inc. "Multi-Language Hubs", memorandum; Publicly available on Apr. 2, 2009.

Initiate, "Business Scenario: Support for Members in Multiple Entities", Publicly available on Oct. 2, 2008.

Initiate, "Group Entities", Publicly available on Mar. 30, 2007.

Jim Cushman, MIO 0.5: MIO As a Source; Initiate; Publicly available on Oct. 2, 2008.

Initiate, "Provider Registry Functionality", Publicly available on Oct. 2, 2008.

Edward Seabolt, "Requirement Specification Feature #NNNN Multiple Entity Relationship", Version 0.1—Draft; Publicly available on Oct. 2, 2008.

Initiate, "Arriba Training Engine Callouts", presentation; Publicly available on Mar. 30, 2007.

Initiate, "Business Scenario: Callout to Third Party System", Publicly available on Oct. 2, 2008.

John Dorney, "Requirement Specification Feature #NNNN Conditional Governance", Version 1.0—Draft; Publicly available on Oct. 2, 2008.

Initiate, Release Content Specification, Identity Hub Release 6.1, RCS Version 1.0; Publicly available on Sep. 16, 2005.

Initiate, "Initiate Identity Hub™ Manager User Manual", Release 6.1; Publicly available on Sep. 16, 2005.

End User Training CMT; CIO Maintenance Tool (CMT) Training Doc; Publicly available on Sep. 29, 2006.

"Hierarchy Viewer—OGT 3.0t", Publicly available on Sep. 25, 2008.

"Building and Searching the OGT", Publicly available on Sep. 29, 2006.

Sean Stephens, "Requirement Specification B2B Web Client Architecture", Version 0.1—Draft; Publicly available on Sep. 25, 2008.

"As of: OGT 2.0", Publicly available on Sep. 29, 2006.

Initiate, "Java SDK Self-Training Guide", Release 7.0; Publicly available on Mar. 24, 2006.

European Communication for EP 07795659 (PCT/US2007013049) dated May 27, 2010.

Initiate, "Memtype Expansion Detailed Design", Publicly available on Apr. 2, 2009.

Ohgaya, Ryosuke et al., "Conceptual Fuzzy Sets-, NAFIPS 2002, Jun. 27-29, 2002, pp. 274-279.Based Navigation System for Yahoo!".

Xue, Gui-Rong et al., "Reinforcing Web-Object Categorization Through Interrelationships", Data Mining and Knowledge Discover, vol. 12, Apr. 4, 2006, pp. 229-248.

Adami, Giordano et al., "Clustering Documents in a Web Directory", WIDM '03, New Orleans, LA, Nov. 7-8, 2003, pp. 66-73.

Chen, Hao et al., "Bringing Order to the Web: Automatically Categorizing Search Results", CHI 2000, CHI Letters, vol. 2, Issue 1, Apr. 1-6, 2000, pp. 145-152.

"Implementation Defined Segments—Exhibit A", Publicly available on Mar. 20, 2008.

Initiate, "Implementation Defined Segments—Gap Analysis", Publicly available on Mar. 20, 2008.

"Supporting Hierarchies", Publicly available on Nov. 29, 2007.

Xue, Gui-Rong et al., "Implicit Link Analysis for Small Web Search", SIGIR '03, Toronto, Canada, Jul. 28-Aug. 1, 2003, pp. 56-63.

Liu, Fang et al., "Personalized Web Search for iMproving Retrieval Effectiveness", IEEE Transactions on Knowledge and Data Engineering vol. 16, No. 1, Jan. 2004, pp. 28-40.

Anyanwu, Kemafor et al. "SemRank: Ranking complex Relationship Search Results on the Semantic Web", WWW 2005, Chiba, Japan May 10-14, 2005, pp. 117-127.

International Preliminary Report on Patentability, PCT/US2008/58404, Mar. 21, 2011, 4 pages.

European Search Report/EP07795659.7, Apr. 15, 2011, 7 pages.

Emdad Ahmed, "A Survey on Bioinformatics Data and Service Integration Using Ontology and Declaration Workflow Query Language", Department of Computer Science, Wayne State University, USA, Mar. 15, 2007, pp. 1-67.

International Preliminary Report, PCT/US2007/089211, Apr. 30, 2012, 6 pages.

European Search Report/EP07795108.5, May 29, 2012, 6 pages.

* cited by examiner

SERVICE PROVISIONING

CROSS-REFERENCE TO RELATED APPLICATIONS

This application claims priority from U.S. Provisional Application No. 60/920,735, filed Mar. 29, 2007, entitled "METHOD AND SYSTEM FOR SERVICE PROVISIONING," which is fully incorporated by reference herein.

TECHNICAL FIELD

This invention relates generally to the association, storage, management or processing of data records, and in particular to providing and creating customizable interfaces for interactions with systems operable to accomplish this association, storage, management or processing of data records.

BACKGROUND

In today's day and age, the vast majority of businesses retain extensive amounts of data regarding various aspects of their operations, such as inventories, customers, products, etc. Data about entities, such as people, products, parts or anything else may be stored in digital format in a data store such as a computer database. These computer databases permit the data about an entity to be accessed rapidly and permit the data to be cross-referenced to other relevant pieces of data about the same entity. The databases also permit a person to query the database to find data records pertaining to a particular entity, such that data records from various data stores pertaining to the same entity may be associated with one another.

A data store, however, has several limitations which may limit the ability to find the correct data about an entity within the data store. The actual data within the data store is only as accurate as the person who entered the data, or an original data source. Thus, a mistake in the entry of the data into the data store may cause a search for data about an entity in the database to miss relevant data about the entity because, for example, a last name of a person was misspelled or a social security number was entered incorrectly, etc. A whole host of these types of problems may be imagined: two separate record for an entity that already has a record within the database may be created such that several data records may contain information about the same entity, but, for example, the names or identification numbers contained in the two data records may be different so that it may be difficult to associate the data records referring to the same entity with one other.

For a business that operates one or more data stores containing a large number of data records, the ability to locate relevant information about a particular entity within and among the respective databases is very important, but not easily obtained. Once again, any mistake in the entry of data (including without limitation the creation of more than one data record for the same entity) at any information source may cause relevant data to be missed when the data for a particular entity is searched for in the database. In addition, in cases involving multiple information sources, each of the information sources may have slightly different data syntax or formats which may further complicate the process of finding data among the databases. An example of the need to properly identify an entity referred to in a data record and to locate all data records relating to an entity in the health care field is one in which a number of different hospitals associated with a particular health care organization may have one or more information sources containing information about their patient, and a health care organization collects the information from each of the hospitals into a master database. It is necessary to link data records from all of the information sources pertaining to the same patient to enable searching for information for a particular patient in all of the hospital records.

There are several problems which limit the ability to find all of the relevant data about an entity in such a database. Multiple data records may exist for a particular entity as a result of separate data records received from one or more information sources, which leads to a problem that can be called data fragmentation. In the case of data fragmentation, a query of the master database may not retrieve all of the relevant information about a particular entity. In addition, as described above, the query may miss some relevant information about an entity due to a typographical error made during data entry, which leads to the problem of data inaccessibility. In addition, a large database may contain data records which appear to be identical, such as a plurality of records for people with the last name of Smith and the first name of Jim. A query of the database will retrieve all of these data records and a person who made the query to the database may often choose, at random, one of the data records retrieved which may be the wrong data record. The person may not often typically attempt to determine which of the records is appropriate. This can lead to the data records for the wrong entity being retrieved even when the correct data records are available. These problems limit the ability to locate the information for a particular entity within the database.

To reduce the amount of data that must be reviewed, and prevent the user from picking the wrong data record, it is also desirable to identify and associate data records from the various information sources that may contain information about the same entity. There are conventional systems that locate duplicate data records within a database and delete those duplicate data records, but these systems may only locate data records which are substantially identical to each other. Thus, these conventional systems cannot determine if two data records, with, for example, slightly different last names, nevertheless contain information about the same entity. In addition, these conventional systems do not attempt to index data records from a plurality of different information sources, locate data records within the one or more information sources containing information about the same entity, and link those data records together. Consequently, it would be desirable to be able to associate data records from a plurality of information sources which pertain to the same entity, despite discrepancies between attributes of these data records and be able to assemble and present information from these various data records in a cohesive manner. In practice, however, it can be extremely difficult to provide an accurate, consolidated view of information from a plurality of information sources. In an enterprise environment, the challenge can be even greater as the logic for business service operations can be arbitrarily complex. Often there is a chasm between business service operations that serve particular business needs and data operations that serve data management needs. Accordingly, there is always room for improvement.

SUMMARY OF THE DISCLOSURE

Embodiments disclosed herein can provide systems and methods that can bridge the gap between business operations and data operations. More particularly, embodiments disclosed herein provide a customizable interface layer for interactions with systems operable to accomplish association, storage, management or processing of data records based on user-defined business service operations. For example, some embodiments disclosed herein may allow a user to define interfaces, services, operations, as well as logical procedures according to a desired data model, such that the inputs and outputs for each operation of the service correspond to the particular needs of the user and allow different terminology to be employed by the user. By allowing a user to define and customize such an interface layer, the MEI system may be used more easily with a client application of the user and may adhere more closely to the particular needs of the user.

Some embodiments disclosed herein interface with a master entity indexer which, in one embodiment, refers to a special software engine that operates with data records from one or more information sources. One embodiment includes service provider logic for providing a set of services, each of which has a set of operations. In one embodiment, each operation is defined by a deployed definition of the service. In one embodiment, each of the operations has an associated logical procedure, also referred to as flow logic, that is customizable (e.g., at deployment or installation time by a manager, a system administrator, a software engineer, or the like). In one embodiment, each service is associated with a corresponding interface. In one embodiment, these interfaces may utilize Simple Object Access Protocol or SOAP interfaces (e.g., SOAP formatted XML envelopes). For example, they may allow queries for a service to be submitted utilizing SOAP.

In one embodiment, a user may submit (e.g., via an interface utilizing SOAP) a query to the service provider logic. The service provider logic provides the query to a service corresponding to that interface. The service, in turn, provides one or more operations which may be accessed using the interface. Thus, based on the operation associated with the query, an operation of the service corresponding to the interface may be selected. Each of the operations 1332 may have a corresponding logical procedure or flow which may be operable to interact with the aforementioned master entity indexer to obtain the set of outputs defined for the operation. The interaction between a logical procedure and the master entity indexer may be through an application programming interface provided by the master entity indexer. In one embodiment, the service may provide inputs in the received query to the logical procedure corresponding to the service, and the logical procedure may then utilize these inputs to obtain corresponding outputs from the master entity indexer.

In one embodiment, each service may be defined by a user using terminologies familiar to the user. This definition of a service may comprise defining a service data model for a service. Such a service data model may comprise a set of data types. The definition of a service may further comprise the definition of one or more of the operations provided by the service, where each operation comprises a set of inputs and desired outputs. Each of the inputs and outputs associated with the operation may be one of the data types associated with the service. The definition of an operation may further comprise the definition of a logical procedure associated with the operation. The definition of this logical procedure may further comprise defining a logical flow for obtaining the desired outputs from the master entity indexer using the set of inputs. The definition of these various logical procedures may occur in almost any manner desired (e.g., graphic based drag-and-drop, text based list-and-select, etc.).

By allowing services according to a service data model to be defined by a user, where each service comprises a set of operations and corresponding logical procedures which may also be defined by the user, the access and provisioning of information with respect to the master entity indexer may be more closely tailored to a particular user's desires and/or business needs.

Other features, advantages, and objects of the disclosure will be better appreciated and understood when considered in conjunction with the following description and the accompanying drawings.

BRIEF DESCRIPTION OF THE DRAWINGS

A more complete understanding of the present invention and the advantages thereof may be acquired by referring to the following description, taken in conjunction with the accompanying drawings in which like numerals are used to refer to like and corresponding parts or elements, wherein.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Preferred embodiments and the various features and advantageous details thereof are explained more fully with reference to the examples illustrated in the accompanying drawings. Descriptions of well known computer hardware and software, including programming and data processing techniques, are omitted so as not to unnecessarily obscure the invention in detail. Skilled artisans should understand, however, that the detailed description and the specific examples, while disclosing preferred embodiments of the invention, are given by way of illustration only and not by way of limitation. Various substitutions, modifications, additions or rearrangements within the scope of the underlying inventive concept(s) will become apparent to those skilled in the art after reading this disclosure.

Some embodiments disclosed herein can leverage an embodiment of a system and method for indexing information about entities from different information source, as described in U.S. Pat. No. 5,991,758, issued Nov. 23, 1999, which is incorporated herein by reference. Some embodiments disclosed herein can leverage an embodiment of a master data management system and method for indexing information about entities with respect to hierarchies, as disclosed in U.S. patent application Ser. No. 11/656,111, filed Jan. 22, 2007, which is also incorporated herein by reference.

In one embodiment, the systems and methods disclosed herein may be particularly useful in a health care setting and thus examples may be described in this context. It will be appreciated, however, that embodiments of the systems and methods disclosed herein have utility in a wide variety of other settings.

Figure 1:
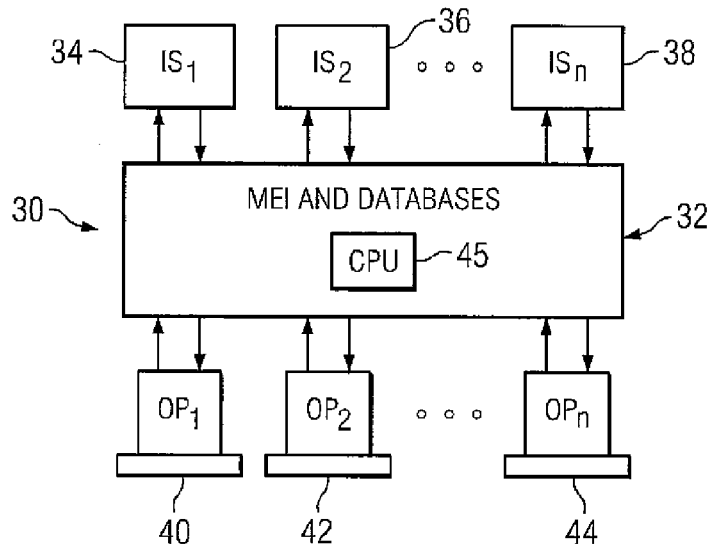
FIG. 1 is a block diagram illustrating one embodiment of a master entity indexer.

To illustrate more clearly, FIG. 1 is a block diagram illustrating a master entity index system 30 in accordance with embodiments of the invention. The master entity index system may include a master entity indexer (MEI) 32 that processes, updates and stores data records about one or more entities from one or more information sources 34, 36, 38 and responds to commands or queries from a plurality of operators 40, 42, 44, where the operators may be either users or information systems. MEI 32 may operate with data records from a single information source or, as shown, data records from one or more information sources. Entities tracked using MEI 32 may include for example, patients in a hospital, participants in a health care system, parts in a warehouse or any other entity that may have data records and information contained in data records associated with it. In one embodiment, MEI 32 may be a computer system with a central processing unit 45 executing a software application that performs the function of MEI 32. In one embodiment, MEI 32 may also be implemented using hardware circuitry.

As shown, in one embodiment, MEI 32 may receive data records from the information sources as well as write corrected data back into the information sources. The corrected data communicated to the information sources may include information that was correct, but has changed, information about fixing information in a data record or information about links between data records. In addition, one of the users 40-44 may transmit a query to MEI 32 and receive a response to the query back from MEI 32. The one or more information sources may be, for example, different databases that possibly have data records about the same entities. For example, in the health care field, each information source may be associated with a particular hospital in the health care organization and the health care organization may use the master entity index system to relate the data records within the plurality of hospitals so that a data record for a patient in Los Angeles may be located when that same patient is on vacation and enters a hospital in New York.

It will be apparent to those of ordinary skill in the art, that both the data sources 34, 36, 38 and the operators 40, 42, 44 may be affiliated with similar or different organizations or owners. For example, data source 34 may be affiliated with a hospital in Los Angeles run by one health care network, while data source 36 may be affiliated with a hospital in New York run by another health care network. Thus, the data records of each of data sources may be of a different format.

Figure 2A:
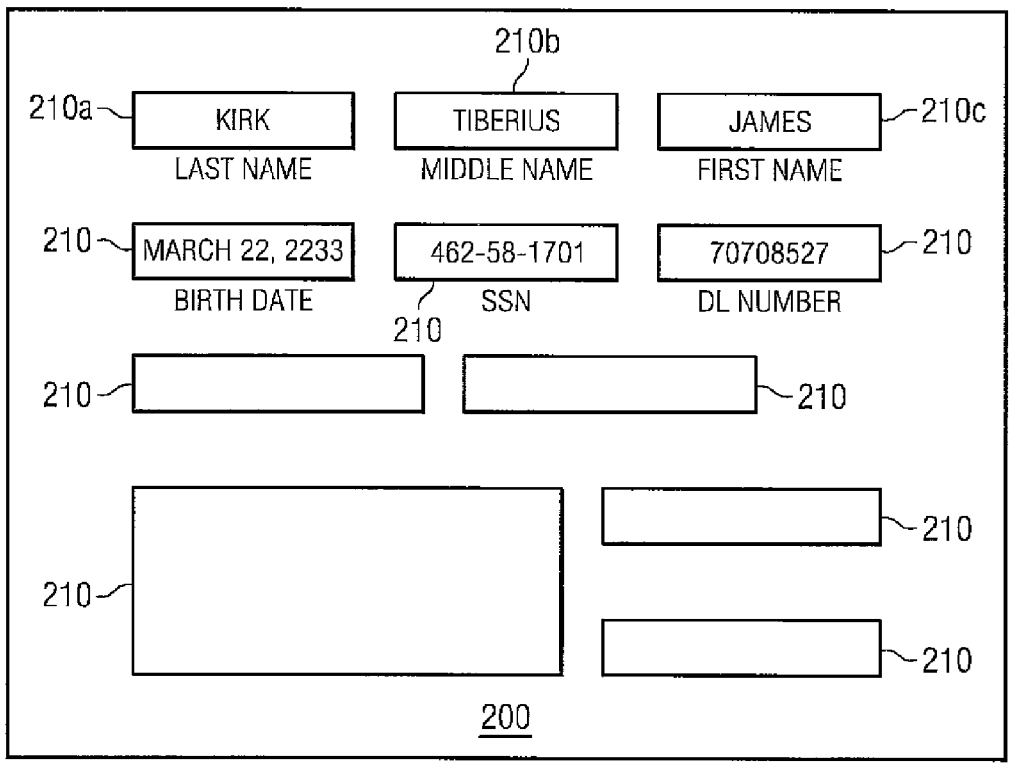
FIGS. 2A and 2B depict two embodiments of example data records.
Figure 2B:
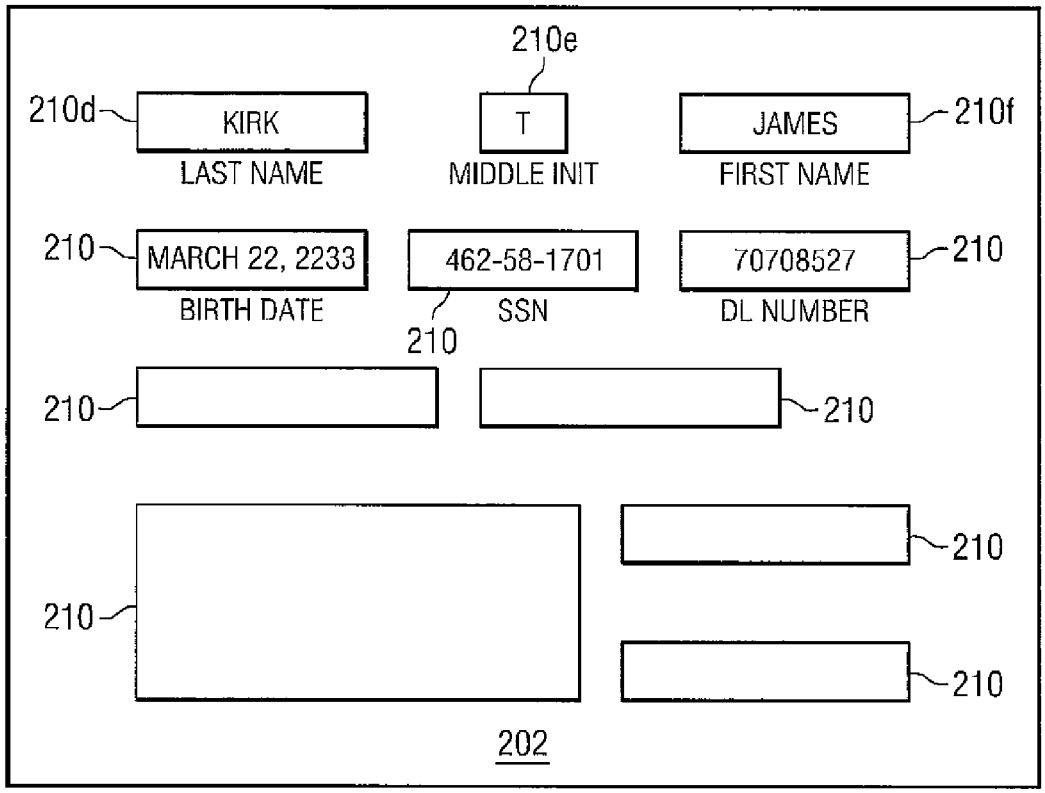

This may be illustrated more clearly with reference to FIGS. 2A and 2B, depicting two embodiments of example data records. Each of these data records 200, 202 has a set of fields 210 corresponding to a set of attributes of each of the data records. For example, one of the attributes of each of the records 200 may be a name, another attribute may be a social security number, birth date, gender, etc. It will be apparent that an attribute may comprise multiple fields 210 of a data record 200, 202, for example, the name attribute of data record 200 may comprise fields 210a, 210b and 210c, the last, middle and first name fields, respectively.

Notice, however, that each of the records may have a different format, for example data record 202 may have a field for the attribute of driver's license number, while data record 200 may have no such field. Similarly, like attributes may have different formats as well. For example, name fields 210a, 210b 210c in record 200 may accept the entry of a full first, last and middle name, while name fields 210d, 210e, 210f in record 202 may be designed for full first and last names, but only allow the entry of a middle initial.

Returning to FIG. 1, MEI 32 of the master entity index system 30 may be located at a central location and the information sources and users may be located remotely from MEI 32 and may be connected to MEI 32 by, for example, a communications link, such as the Internet. MEI 32, the one or more information sources and the plurality of users may also be connected together by a communications network, such as a wide area network. MEI 32 may have its own database that stores the complete data records in MEI 32, but MEI 32 may also only contain sufficient data to identify or locate a data record (e.g., an address in a particular information source or an information source associated with the data record) or any portion of the values of the data fields that comprise a complete data record so that MEI 32 retrieves the entire data record, or portions thereof, from the information source when needed. MEI 32 may link data records together containing information about the same entity in an entity identifier or associative database, as described below, separate from the actual data record. Thus, MEI 32 may maintain links between data records in one or more information sources, but does not necessarily maintain a single uniform data record for an entity. Now, an example of the master entity index system in accordance with embodiments of present the invention will be described.

Figure 3:
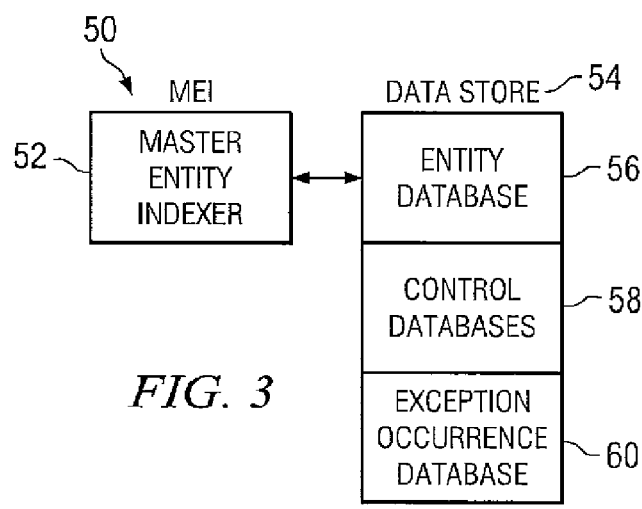
FIGS. 3 and 4 are block diagrams illustrating embodiments of a master entity index system.

FIG. 3 is a block diagram illustrating an example of a master entity index system for a health care, or other, organization. In this example, master entity index system 50 may include master entity indexer (MEI) 52 and data store 54. For clarity, information sources and multiple users are not shown, but are connected to MEI 52 in a manner similar to MEI 32 as previously described. Data store 54 may include entity database 56, one or more control databases 58, and an exception occurrence database 90. Such an entity database may store data from the data records as specified above from the one or more information sources. The entity database may also separately store links between one or more data records when those data records contain information about the same entity. The entity database may also store an address of a large data record stored in one of the information sources to reduce the storage requirements of the entity database. In one example, the information about entities within the data records may be information about patients within a plurality of hospitals which are owned by a health care organization. MEI 52 may process the data records from the one or more information sources located at each hospital, identify and associate records that contain information about the same entity, and generate the links between the separate data records when the data records contain information about the same patient.

As data records from the information sources are fed into the MEI, the MEI may store the incoming data record or portions thereof in the entity database according to a member type definition and may also attempt to match the incoming data record about an entity to a data record already located in the MEI database (referred to as member data records). If the incoming data record matches an existing data record, a link between the incoming data record and the matching data record may be generated. If the incoming data record does not match any of the existing data records in the MEI, a new entity identifier, as described below, may be generated for the incoming data record. Then as additional data records are received from the information sources, these data records are matched to existing data records and the MEI database of data records is increased.

The one or more control databases 58 may be used by the MEI to control the processing of the data records to increase accuracy. For example, one of the control databases may store rules which may be used to override certain anticipated erroneous conclusions that may normally be generated by the MEI. For example, the operator of the MEI may know, due to experience, that the name of a particular patient is always misspelled in a certain way and provide a rule to force the MEI to associate data records with the known different spellings. The control databases permit the operator to customize the MEI for a particular application or a particular type of information. Thus, for a health care system containing information about a patient, the control databases may contain a rule that the nickname "Bill" is the same as the full name "William." Therefore, the MEI will determine that data records otherwise identical except for the first name of "Bill" and "William" contain information about the same entity and should be linked together. Embodiments of the MEI will now be described in more detail.

Figure 4:
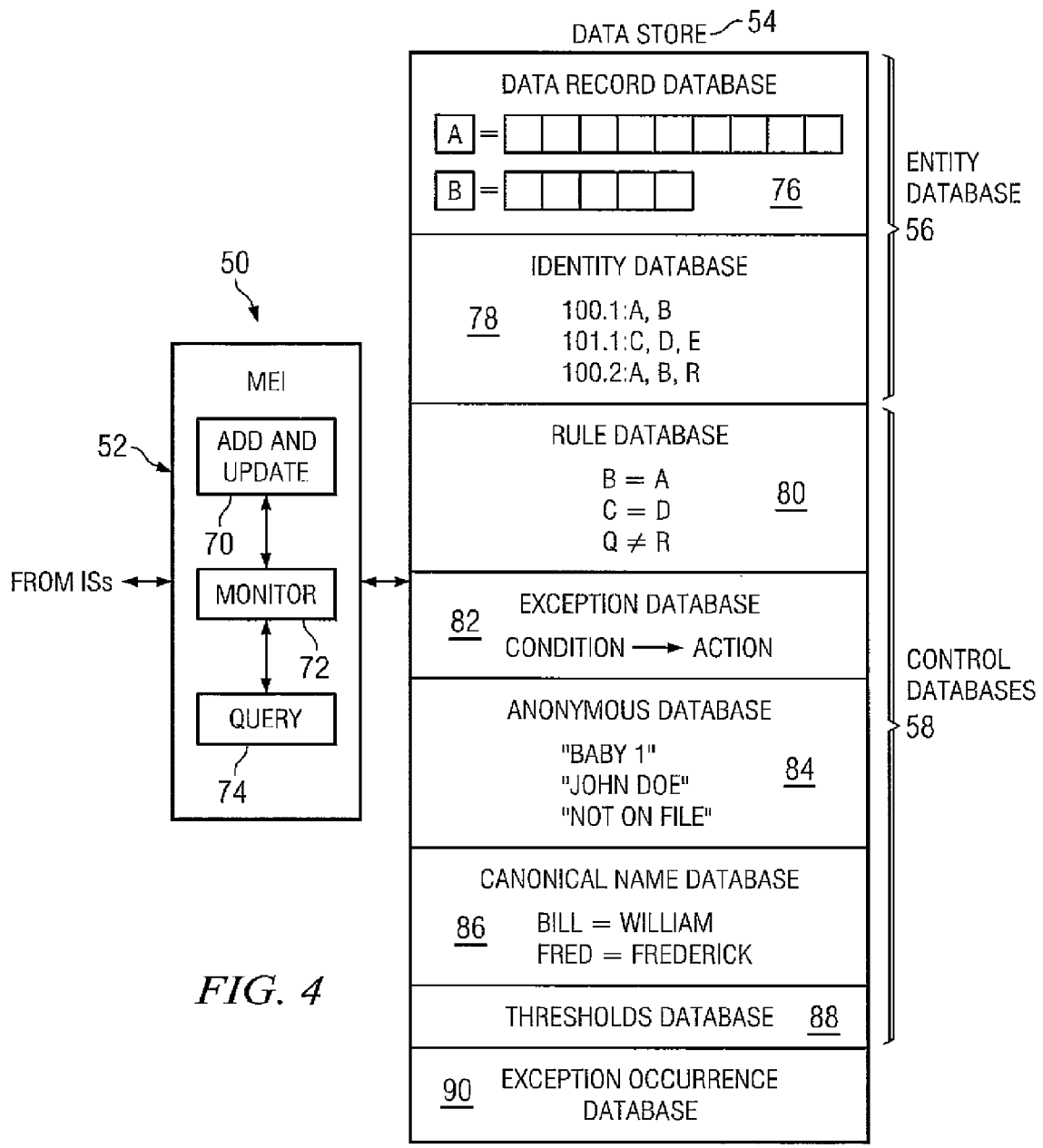

FIG. 4 is a block diagram illustrating more details of master entity index system 50, and in particular MEI 52 and data store 54. MEI 52 may include addition and updating unit 70, monitor unit 72 and query unit 74. Addition and updating unit 70 may add data records about a new entity into data store 54, update data records in data store 54, or add new rules to control databases 58. Monitor unit 72 may permit a user of master entity index system 50 to view special conditions, known as exceptions, generated by MEI 52. For example, a data record that requires a person to view the data record due to an error may be tagged and a message to the operator may be generated. Query unit 74 permits a user of master entity index system 50 to query MEI 52 about information in the data records or information in control databases 58 of MEI 52 and MEI 52 will return a response to the query including any relevant data records or information. More details of these units and their associated functions will be described below.

For each of the operations of the MEI, including the synthesis, as described below, the querying and the monitoring, the results of those operations may depend on a trust value that may be associated with each data field in a data record. The trust computation for a data field may vary depending on the characteristics of the data field, such as the date on which that data record containing the field was received, or a quantitative characterization of a level of trust of the information source. For example, a data field containing data that was manually entered may have a lower trust value than a data field with data that was transferred directly from another information source. The trust value for a data field may also affect the probability of the matching of data records. Now, data store 54 of master entity index system 50 will be described in more detail.

MEI 52 may provide other operations that can be constructed from combining the operations listed above. For example, an operation to process data records for which it is not known if a data record exists can be constructed by combining the query operation for data records with the add new data record or update existing data record operations. These "composite" operations may lead to better performance than if the operator executed a combination of the basic operations. They also relieve the operator for having to determine the correct sequencing of operations to achieve the desired result.

Data store 54 may include an entity database 56, one or more control databases 58, and exception occurrence database 90 as described above. Entity database 56 may include data record database 76 and identity database 78. Data record database 76 may store the data records or the addresses of the data records in MEI 52, as described above, while associative identity database 78 may store a group of data record identifiers that associate or "link" those data records which contain information about the same entity. The separation of the physical data records from the links between the data records permits more flexibility because a duplicate copy of the data contained in the data record is not required to be present in the identity database. Data record database 76 and associative identity database 78 may also be combined if desired.

In one embodiment, the data record database may be configured according to one or more member type definitions where each member type definition which comprises a set of attributes of data records which are stored and managed in an MEI system. The attributes of the member type definition may be grouped into identity data which comprises those attributes whose values are stored in data record database in conjunction with a data record. Conversely, non-identity attributes may be attributes whose values are not stored in data record database, and which may or may not be encompassed by the member type definition. For example, in a healthcare setting member type definition may comprise "Person", which is commonly used in a healthcare environments to accommodate management of person/patient data; "Provider", which is commonly used in healthcare provider/payor environments to accommodate management of network provider (e.g., medical centers, doctors, laboratories, etc.) data; "Guest", which is used in the hospitality environment to accommodate the management of guest/frequent guest data and "Company", which is used most often in non-healthcare environments, typically to manage information about companies rather than or in addition to information about customers.

For each data record corresponding to a member type definition, then, the set of identity information from the data record corresponding to that member type definition may be stored in a data record database along with a reference to an information source or location corresponding to the data record (e.g., the location of a data record in an information source from to which the member data record corresponds). It will be noted here that, for each member type definition, a different set of identity information (e.g., attributes) may be specified, and that only as much identity information corresponding to the member type definition as is available for that data record may be stored. For example, if a data record corresponds to a member type of "Person" the values for the name and address attributes of the data record may be stored in data record database if they are available. Furthermore, historical values may be stored for each of the identity attributes. For example, if a member type definition comprises an address attribute, a first address value may be stored for a member in data record database. At some later point the member data record (e.g., a data record corresponding to the member data record) may be updated with a new address. At this point the value for the address associated with the member data record may be updated to the new address and the first address value stored as a historical value for the address attribute associated with that member. It will be noted that the number of historical values for each identity attribute may differ according to the identity attribute and may be as few or as many as desired in a given embodiment of the present invention.

The identity database represents the combination of data records in the data record database that refer to the same entity. Each entity is assigned an entity identifier. Entity identifiers are based on the concept of "versioned" identification. An entity identifier consists of a base part and a version number. The base part represents a specific individual about whom information is being linked. The version number represents a specific combination of data records that provides information about the entity that is known at a specific time. In this example, the data records are shown as squares with the alphabetic identifier of the data record inside, and the entity identifier is shown as the base part followed by a period followed by a version number. For example, "100.0" indicates an entity identifier with 100 as the base part and 1 as the version number. In this example, entity identifier 100.0 links data records A and B, entity identifier 101.0 links data records C, D and E, and entity identifier 101.1 links data records A, B, and R. Now, the details of the control databases will be described.

In one embodiment, one or more control databases of an MEI may permit the operator of a master entity index system to customize the MEI's processing based on information known to the operator. The control databases shown are merely illustrative and the MEI may have additional control databases which further permit control of the MEI by the operator. The control databases may, for example, include rules database 80, exception handling database 82, anonymous name database 84, canonical name database 86, and thresholds database 88.

The rules database may contain links that the operator of the system has determined are certain and should override the logic of the matching of the MEI. For example, the rules database may contain identity rules (i.e., rules which establish that a link exists between two data records) and/or non-identity rules (i.e., rules which establish that no link exists between two data records). In this example, the rules database contains identity rules which are A=B and C=D and a non-identity rule which is Q.notequal.R. These rules force the MEI to establish links between data records or prevent links from being established between data records. For example, the information sources may have four patients, with data records S, T, U, and V respectively, who are all named George Smith and the operator may enter the following nonidentity rules (i.e. S.notequal.T, T.notequal.U, U.notequal.V, V.notequal.S) to keep the data records of the four different entities separate and unlinked by the MEI. The rules in the rules database may be updated, added or deleted by the operator of the master entity index system as needed.

The exception handling database 82 contains one or more exception handling routines that permit the master entity index system to handle data record problems. The exception handling rules within the database may have the form of "condition.fwdarw.action" processing rules. The actions of these rules may be actions that the MEI should automatically take in response to a condition, for example, to request that an individual manually review a data record. An example of an exception handling rule may be, "if duplicate data record.fwdarrow.delete data record" which instructs the MEI to delete a duplicate data record. Another example is, "if different attributes (sex).forwardarrrow.request further review of data record" which instructs the MEI that if there are two data records that appear to relate to the same entity, but the sex of the entity is different for each data record, the MEI should request further review of the data records. In response to this request, an operator may determine that the data records are the same, with an incorrectly typed sex for one of the records and the operator may enter a rule into the rules database that the two data records are linked together despite the difference in the sex attribute. The exception database may have an associated database 80 (described below) which stores the actual exceptions that occur during processing of the input data records.

In one embodiment, an anonymous name database (e.g., anonymous name database 84) may permit the MEI to automatically recognize names that should be ignored for purposes of attempting to match two data records. In this example, the anonymous name database may contain "not on file", "John Doe" and "baby.subtext.--1" which are names that may be typically assigned by a hospital to a patient when the hospital has not yet determined the name of the patient. As another example, a part not in a warehouse inventory may be referred to as "not on file" until the part may be entered into the database. These anonymous names may be used by the MEI to detect any of the anonymous names or other "filler" data that hold a space, but have no particular meaning in data records and ignore those names when any matching is conducted because a plurality of data records containing the name of "John Doe" should not be linked together simply because they have the same name.

In one embodiment, a canonical name database (e.g., canonical name database 86) may permit the MEI to associate short-cut data, such as a nickname, with the full data represented by the short-cut data, such as a person's proper name. In this example for a health care organization, the nickname Bill may be associated with William and Fred may be associated with Frederick. This database permits the MEI to link together two data records that are identical except that one data record uses the first name Bill while the second data record uses the first name William. Without this canonical name database, the MEI may not link these two data records together and some of the information about that patient will be lost. The thresholds database 88 permits the thresholds used by the MEI for matching data records, as described below, to be adjustable. For example, an operator may set a high threshold so that only exact data records are matched to each other. A lower threshold may be set so that a data record with fewer matching data fields may be returned to the user in response to a query. The details of the matching method will be described below in more detail.

In one embodiment, an exception occurrence database (e.g., exception occurrence database 90) may allow the MEI to maintain a record of all of the exceptions that have occurred. The exception occurrence database may store the actual exception conditions that have arisen during processing. For example, the exception occurrence database may contain an entry that represents that entity 100.2 has two data records with different values for the "sex" attribute.

In one embodiment, the operator of the MEI may clear identity database 78 without clearing data record database 76. Thus, an operator may have the MEI receive a plurality of input data records and generate a plurality of links with a particular matching threshold level, as described below, being used. The operator may then decide to perform a second run through the data using a lower matching threshold level to produce more links, but does not want to delete the data records themselves, and does not want to delete the identity and non-identity rules from the rules database created during the first run through the data. Thus, the operator may delete the identity database, but keep the control databases, and in particular the rules database, for the second run through the data.

As discussed above, a query unit permits a user of a master entity index system to query an MEI thereof about information in data records or information in the control databases of the MEI and the MEI will return a response to the query including any relevant data records or information. In one embodiment, for example, a user may query the MEI utilizing one or more criteria and the MEI will respond to the query with data corresponding to a set of member data records determined based on the criteria. More particularly, MEI may provide an application programming interface (API) such that a user may submit a query comprising one or more criteria and the MEI utilize the criteria to obtain a response to the query, where the response comprises a set of member data records, and return data corresponding to these member data records to the user.

Figure 12:
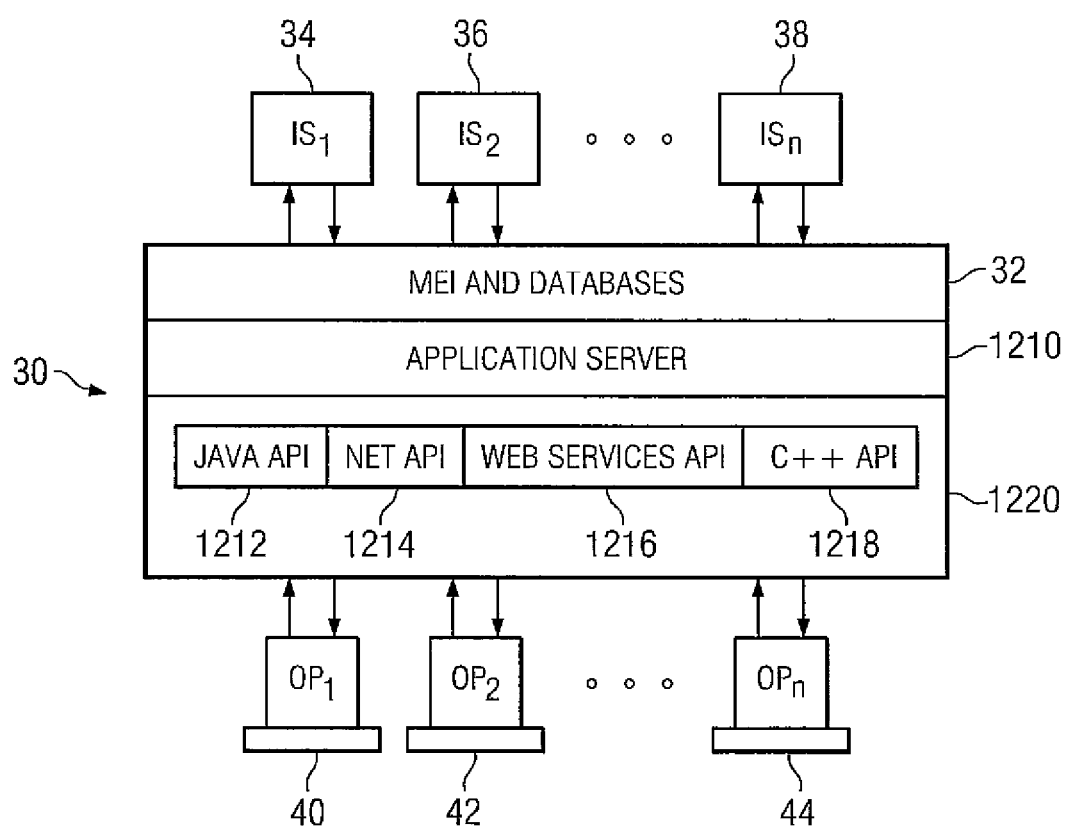
FIGS. 12 and 13 are block diagrams illustrating embodiments of providing interfaces for interactions with a master entity indexer.

Referring to FIG. 12, an embodiment of providing interfaces for interaction with an MEI is presented. MEI 32 may be coupled to application server 1210 (e.g., application server 1210 may be executing in conjunction with MEI 32 or on one or more standalone computing devices in communication with MEI 32, etc.). Application server 1210 may provide one or more application programming interfaces (APIs), such as Java API 1212, .NET API 1214, Web Services API 1216, C++API 1218. In FIG. 12, these APIs reside at API layer 1220. One skilled in the art will appreciate that these APIs are exemplary only and that application server 1210 may provide just about any type of API either proprietary or standardized.

Thus, operators may interact with MEI 32 by submitting a query according to one or more of the APIs provided by application server 1210, MEI 32 may process the query, and the result of the query is returned to the user according to the API with which the query was submitted. This mode of interaction, or interfacing, with MEI 32 may be problematic in certain cases, however. First, MEI 32 may have a great deal of functionality, thus APIs provided to interface with MEI 32 may be correspondingly complex. In many cases, users develop client applications which utilize functionality provided by MEI 32 to implement desired functionality specific to a user. As the APIs provided by MEI 32 may be quite complex, development of these client applications may be similarly complicated. Furthermore, as these APIs may be quite powerful, exposing these APIs to client application which may be potentially buggy, or to possibly malicious programs, may likewise be undesirable.

Additionally, in some embodiments, these APIs may only conform to a data model provided by MEI 32. This data model may correspond to a data model utilized by MEI 32 to store or represent data internally (e.g., in data store 54). Thus, the data model provided through APIs for interfacing with MEI 32 may not correspond to a data model desired by a user. Moreover, APIs provided by MEI 32 may only return a limited set of data, such that a user may have to utilize two or more queries to obtain desired data. In some cases, MEI 32 may return more data than the user needed and thus requiring the user to perform further processing of the result in order to obtained desired data.

A user may therefore desire to utilize a data model that correspond more closely to their particular needs and desires (e.g., for business purposes), to be able to access data in, or otherwise query, MEI 32 according to this data model, and to be able to query MEI 32 with a particular set of inputs and receive a response comprising a particular set of outputs.

Attention is now directed to embodiments of systems and methods for providing interfaces for interactions with an MEI. Embodiments of these systems and methods may provide an interface layer between operators (e.g., users, managers, system administrators, programmers, etc.) and the MEI. Embodiments disclosed herein may allow an operator to define components of the interface layer including interfaces, services, operations, and/or associated logical procedures according to a desired data model, such that the set of inputs and outputs for each operation of the service correspond to the particular needs of the operator and may utilize a data model and/or terminology employed by the operator. By allowing a human user to define and customize various components, the interface layer may be used more easily with client applications of the user and may adhere more closely to the specific terminology employed by the user.

Figure 13:
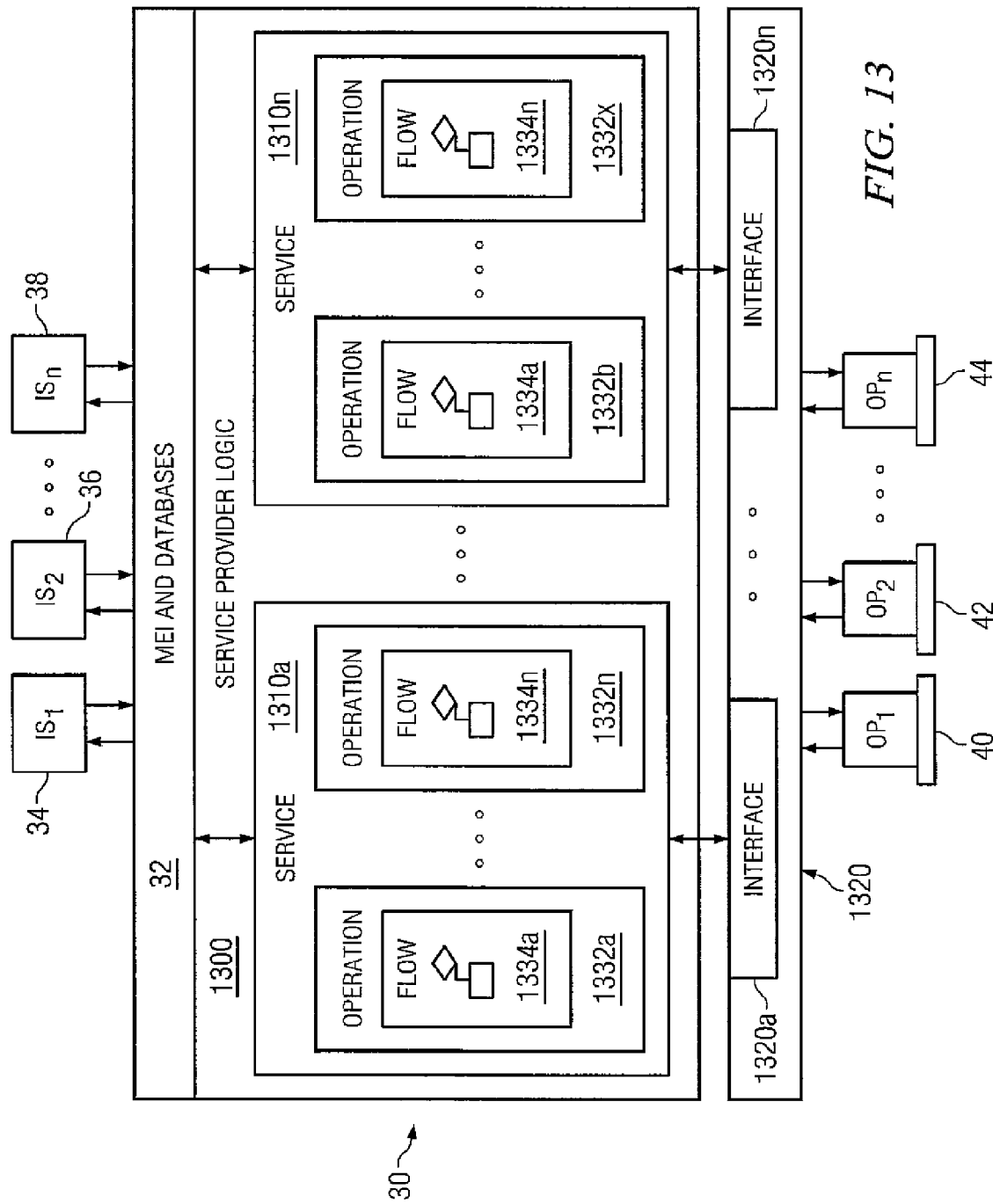

FIG. 13 is a block diagram depicting one embodiment of an interface layer comprising service provider logic 1300 interfacing MEI 32 and operation interface layer 1320 interfacing operators (e.g., operators 40, 42, 44, etc.). Service provider logic 1300 may comprise a set of services 1310a . . . 1310n, each of which is defined according to a particular data model. A data model may be predefined as part of system 30 or defined by an operator. Operation interface layer 1320 may comprise a set of interfaces 1320a . . . 1320n. Each service may be associated with an interface and comprise a set of operations (e.g., service 1310a comprises operations 1332a . . . 1332n, service 1310n comprises operations 1332b . . . 1332x, etc.). Each of these operations may, in turn, be associated with a logical procedure. In FIG. 13, the logical procedures are exemplified by flow 1334a . . . 1334n. The logical procedures need not have graphical representations and can be presented to operators in other ways (e.g., selectable links representing pieces of code). When a query from an operator is received via an interface, a service and an operation of the service corresponding to the interface may be determined and the logical procedure corresponding to the operation invoked to interact with MEI 32 to obtain a set of desired outputs for operation and these outputs returned to the operator via the interface.

In one embodiment, each interface 1320 may adhere to the World Wide Web Consortiums definition of a set of web services which may be implemented by services 1310. In one embodiment, for example, interfaces 1320 may utilize Simple Object Access Protocol (SOAP) interfaces and may be described, or descriptions of the interfaces provided in, Web Services Definition Language (WSDL) (e.g., which may have been deployed). For example, in one embodiment, interface 1320a may allow queries to be submitted utilizing SOAP for service 1310a which can provide a set of operations 1332a . . . 1332n as defined by a deployed definition of service 1310a. Each of operations 1332a . . . 1332n may have a corresponding logical procedure which may be operable to interact with MEI 32 to obtain the set of outputs defined for the particular operation.

SOAP is an XML based protocol for exchanging information in a distributed environment and includes an envelope that defines a framework for describing what is in a message and how to process it, a set of encoding rules for expressing instances of application-defined data types, and a convention for representing remote procedure calls and responses. SOAP may be used in combination with a variety of other protocols and does not itself define application semantics such as a programming model or implementation of specific semantics.

Thus, users may use an interface to submit a query (e.g., utilizing SOAP) to service provider logic 1300 which, in turn, provides the query to the service corresponding to that interface. The service may, in turn, provide one or more operations associated therewith which may be accessed using the interface. Based on the desired operation associated with the query, a particular operation (e.g., operation 1332*a*) of the service (e.g., service 1310*a*) corresponding to the interface (e.g., interface 1320*a*) may be selected. In this case, operation 1332*a* has a corresponding logical procedure 1334*a* operable to interact with MEI 32 to obtain the set of outputs defined for operation 1332*a*. The interaction between logical procedure 1334*a* and MEI 32 may be through API provided by MEI 32 as discussed above or by some other methodology. In one embodiment, service 1310*a* may provide inputs in the received query to logical procedure 1334*a* corresponding to service 1310*a*, and logical procedure 1334*a* may utilize these inputs to obtain corresponding outputs from MEI 32.

In one embodiment, each service may be defined by a user (e.g., using a graphical user interface or the like) such that the defined service may adhere more closely to the needs of the user. This definition of a service may comprise defining a service data model for the service, where the service data model may comprise a set of data types (e.g., associated names and a type of value for that name). The definition of a service (e.g., service 1310*a*) may further comprise the definition of one or more of the operations provided by the service, where each operation comprises a set of inputs and desired outputs, where each of the inputs and outputs associated with the operation may be one of the data types associated with the service. The definition of an operation may further comprise the definition of a logical procedure associated with the operation, where the definition of this logical procedure may comprise defining a flow for obtaining the desired outputs from MEI 32 using the set of inputs. The definition of these various logical procedures may also occur in almost any manner desired.

In one embodiment, for example, a user may utilize a graphical interface to define interfaces 1320*a* . . . 1320*n*, services 1310*a* . . . 1310*n*, operations 1332*a* . . . 1332*n*, and/or logical procedures 1334*a* . . . 1334*n*. The graphical interface may offer a set of visual representations of functionality which the user may utilize to assemble and/or create graphical representations of these components. Interfaces 1320*a* . . . 1320*n*, services 1310*a* . . . 1310*n*, operations 1332*a* . . . 1332*n*, and/or logical procedures 1334*a* . . . 1334*n* may then instantiate from the graphical representation created by the user. These components (i.e., interfaces 1320, services 1310, operations 1332, and logical procedures 1334) may also be hard coded during installation or configuration of MEI 32, or provided by one or more third party vendors. By allowing services according to a service data model to be defined by a user, where the service comprises a set of operations and corresponding logical procedures, the access and provisioning of information with respect to the MEI may be more closely tailored to a particular a user's desires or business needs.

Thus, in comparison with FIG. 12, operators in embodiments implementing system 30 of FIG. 13 can now interact with MEI 32 via services 1310 created in the interface layer as illustrated in FIG. 13, instead of through one of the APIs provided by application server 1210 as described above with reference to FIG. 12. Services 1310 may be web services accessible by the operators through a Web Service WSDL over SOAP. Any client technology (e.g., Java, .net, tools such as SoapScope, etc.) that supports web services can consume the WSDL implementing embodiments disclosed herein. One advantage is that since services 1310 can be created based on user defined data model(s) (e.g., via a model wizard, a model editor, or the like), operators need not have knowledge of the underlying logic model employed by MEI 32. Also, as inputs and outputs to operations 1332 of services 1310 can be based on custom, user defined data model(s), they would be familiar to the operators, reducing time and thus cost associated with creating and utilizing services 1310. In some embodiments implementing system 30 of FIG. 13, operators can define and tie operations 1332 to their business logic using flows 1334 (e.g., via an operation wizard, an operation editor, or the like). In some embodiments, certain operations 1332 may be deployed as part of system 30. Flows 1334 can invoke functionality of MEI 32 by making calls to MEI 32. In addition, flows 1334 can manipulate results from MEI 32 to generate appropriate outputs (e.g., objects) that satisfy the underlying business logic. In some embodiments, certain flows 1334 may be automatically created for an operator. In some embodiments, complex logic orchestrations can be created by invoking third party web services in addition to interactions with MEI 32.

Examples of specific features implementing some embodiments disclosed herein will now be described with reference to FIGS. 14-21. One skilled in the art will appreciate that virtually unlimited implementations of these examples may be made without departing from the scope of the embodiments disclosed herein.

Figure 14:
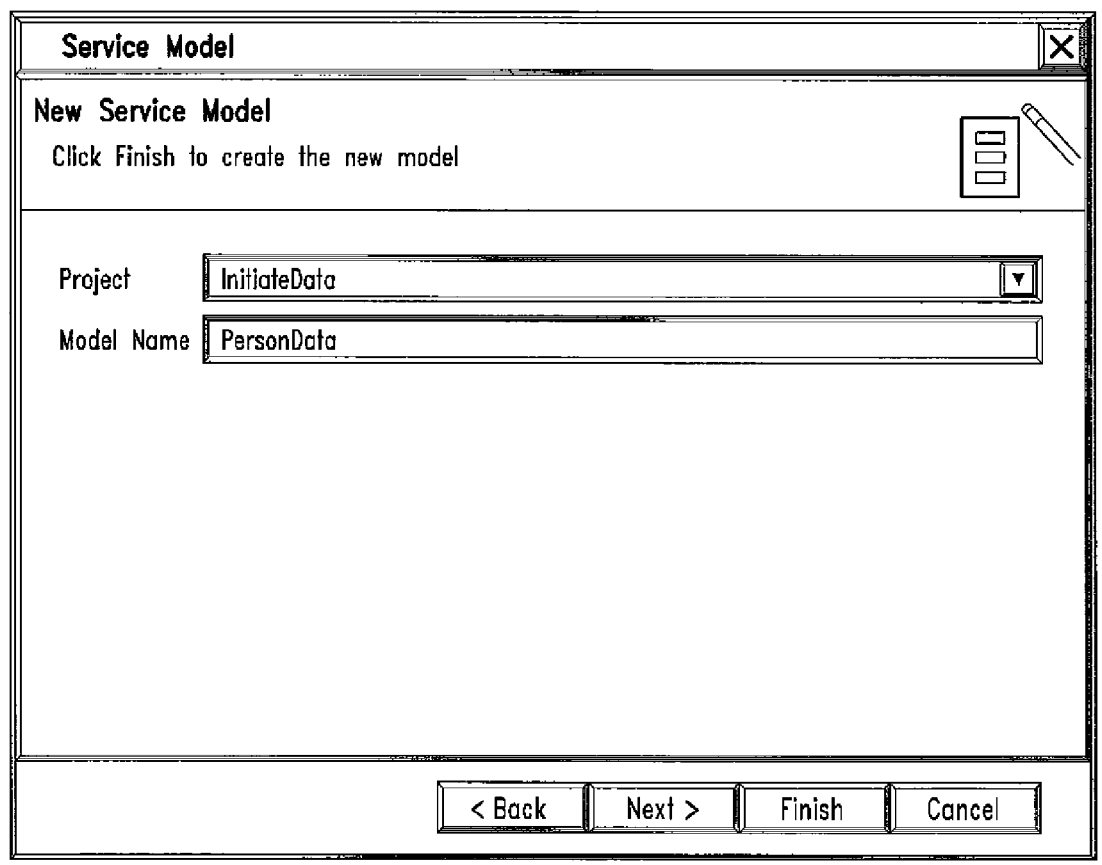
FIG. 14 is a screenshot depicting one example of a Service Model wizard implementing one embodiment in which a new business service model can be created by a user.

FIG. 14 is a screenshot depicting one example of a Service Model wizard implementing one embodiment in which a new custom data model can be created by a user. In this example, a custom data model created by a user is referred to as a Service Model and the logical model employed by MEI 32 is referred to as a Member Model. As described above, a Service Model can be used to define multiple service operations. In defining a Service Model, the user can determine how the new Service Model should be grouped. For example, the user may determine that the new Service Model named "PersonData" is to be grouped under Project InitiateData. In an embodiment, the Service Model wizard may default a new Service Model to a current project that user is working on. In this case, the name of the Service Model, "PersonData", describes the type of data the model will represent.

Figure 15:
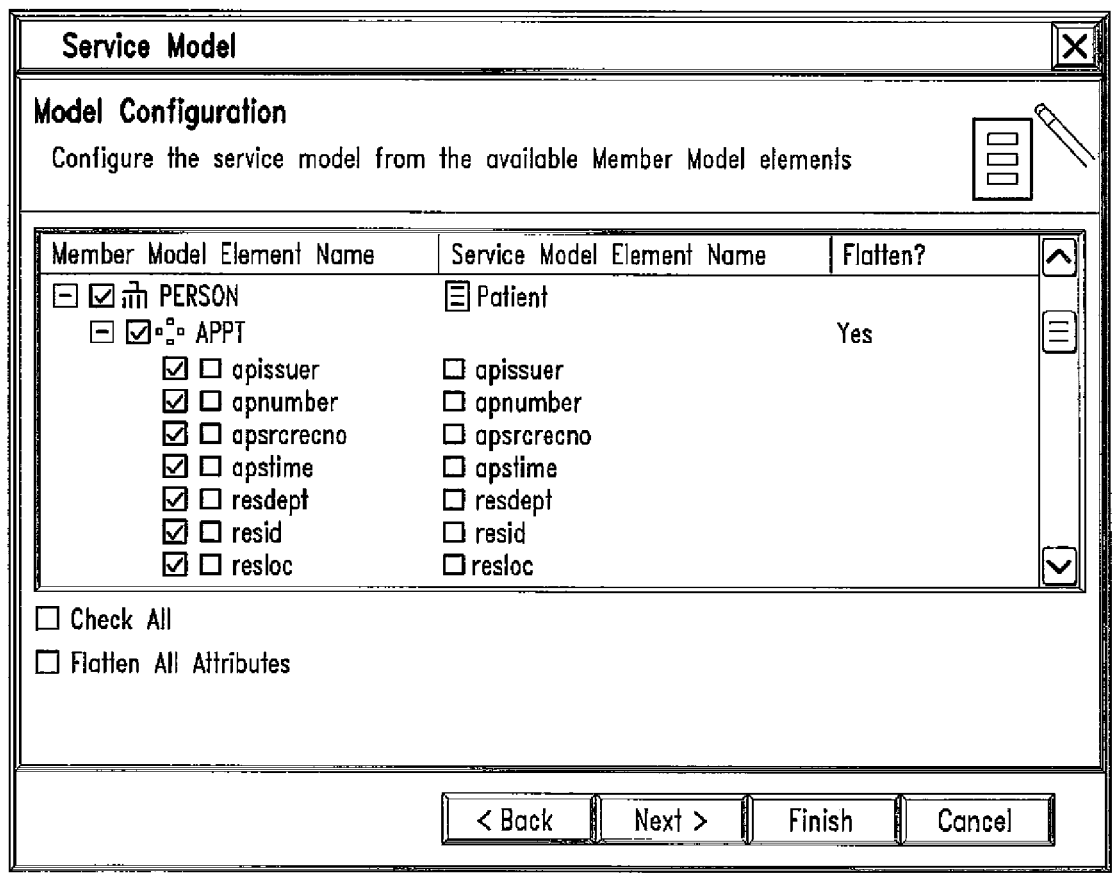
FIG. 15 is a screenshot depicting one example of an embodiment in which a new business service model is configured by a user.

FIG. 15 is a screenshot depicting one example of an embodiment in which a new custom data model is configured by a user. In this example, the Service Model wizard displays a Model Configuration page after the user selects "Next" shown in FIG. 14. On the Model Configuration page, the user can select elements from the Member Model that the user wants the Service Model to represent. If desired, the user can change the name of an element in the "Service Model Element Name" column, perhaps using a different terminology that is more appropriate in a particular environment. As an example, in FIG. 15 the "PERSON" in the "Member Model Element Name" column is changed to "Patient" in the "Service Model Element Name" column. In one embodiment, the Service Model wizard may enable the user to roll all attributes up into a parent object by selecting "Flatten All Attributes." In one embodiment, the Service Model wizard may enable the user to select and roll certain attributes up into a parent object by allowing the user to change the "Yes" or "No" value in the "Flatten?" column. The user can then select "Finish" to generate the service model. In one embodiment, the newly generated service model is represented by a View Logical Model file.

Figure 16:
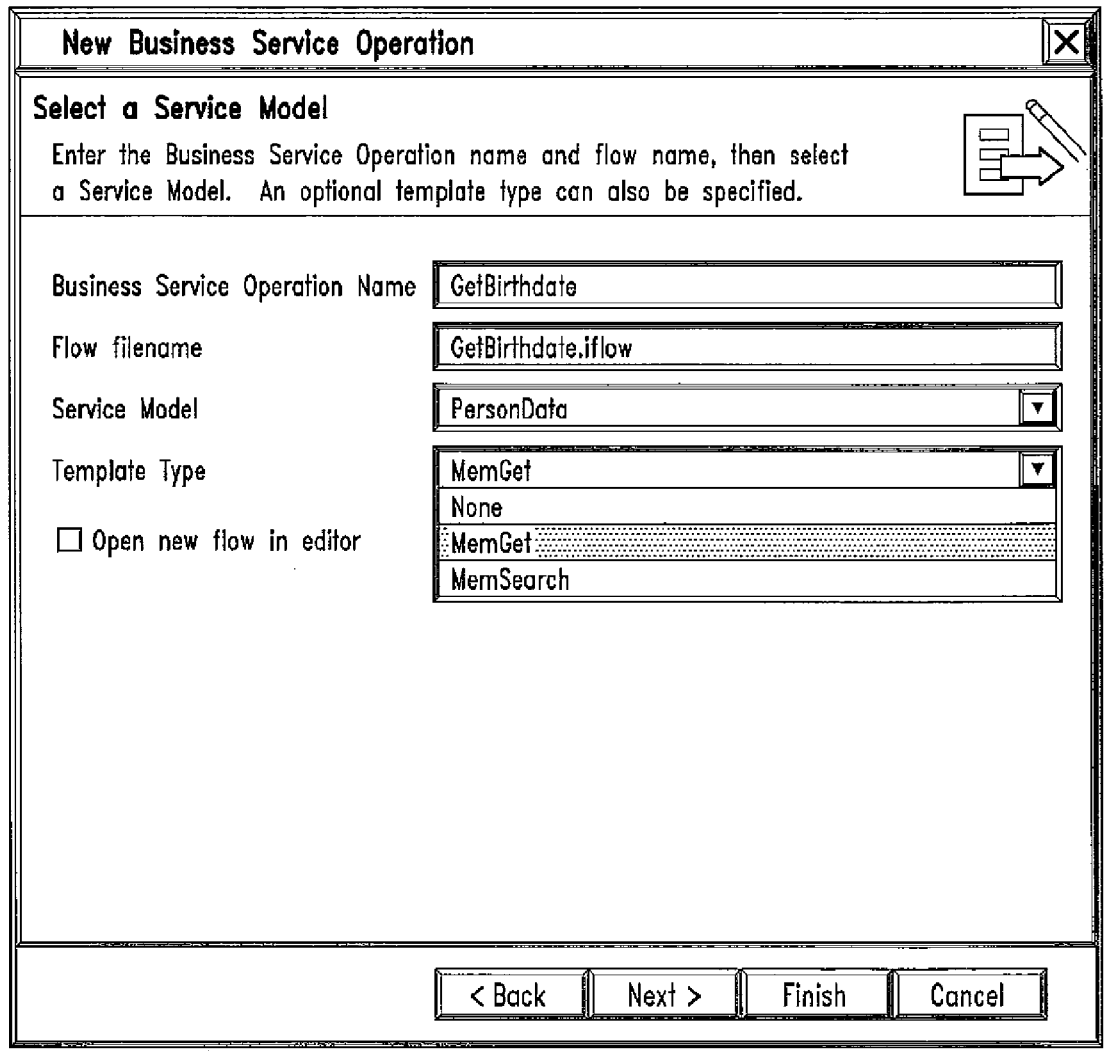
FIG. 16 is a screenshot depicting one example of a New Business Service Operation wizard implementing one embodiment in which a new business service operation can be created by a user based on a business service model that is also created by the user.

FIG. 16 is a screenshot depicting one example of a New Business Service Operation wizard implementing one embodiment in which a new business service operation can be created by a user based on a custom data model that is also created by the user. In some cases, the New Business Service Operation wizard may enable the user to select a project or group that user is currently working on. Following the example of FIG. 14, suppose the user is working on a project named "InitiateData," the New Business Service Operation wizard may enable the user to select "InitiateData" (e.g., from a drop-down list). The user can then provide a name of a service operation that the user wants to create. In one embodiment, as the user enters the name of the service operation, a flow filename is automatically created using the name of the service operation followed by an extension. This default filename can be editable. As an example, FIG. 16 shows a business service operation name "GetBirthdate" and a Flow filename automatically created and displayed to the user as "GetBirthdate.iflow." The user then selects a service model on which the user wants to base the flow (e.g., the exemplary Service Model of "PersonData" of FIG. 14). The field "Template Type" allows the user to select or specify what type of service to use for the flow. In the example shown in FIG. 16, a drop-down list shows three options: "None," "MemGet," and "MemSearch." When selected, "None" creates an empty flow with "hooks" for adding MemGet, MemSearch, or other business logic, perhaps including third party business logic. When selected, "MemGet" performs a get (i.e., retrieve data) operation from MEI 32 (e.g., from a database of MEI 32). When selected, "MemSearch" performs a search (i.e., find data) operation via the MEI (e.g., on a database of MEI 32). In this example, the New Business Service Operation wizard provides a link to open a new flow in an editor. Other ways to access the functionality of the flow editor are also possible. The user then selects "Next" to further configure the service operation or "Finish" to exit.

Figure 17:
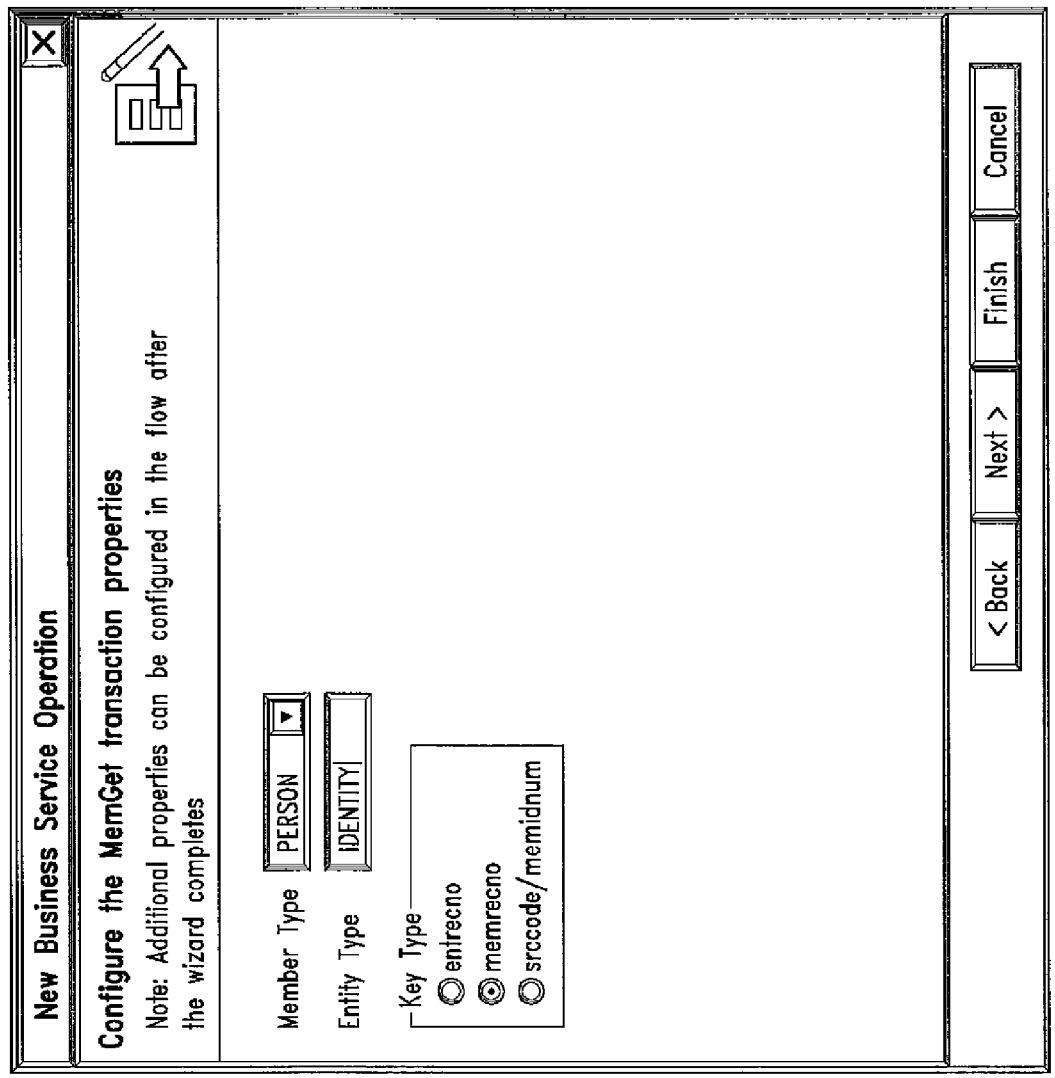
FIG. 17 is a screenshot depicting one example of how a business operation can be configured by a user.

FIG. 17 is a screenshot depicting one example of how a business operation can be configured by a user. In this case, the New Business Service Operation wizard provides a transaction properties page through which the user can configure the MemGet, MemSearch, or other types of services. Configuration information provided through the transaction properties page can be automatically incorporated in the underlying flow logic. Additional properties can also be configured in the flow after the New Business Service Operation wizard completes creating the business operation. The user may select a member type based on the type of data contained in the service model. As an example, the user may select "PERSON" as a member type based on the type of data contained in the service model "PersonData." The user may then select or type the name of the entity type (e.g., IDENTITY, HOUSEHOLD, etc.) that the user wants the business operation (e.g., MemGet, MemSearch, etc.) to use. In this example, the MemGet flow has three key type options: entity record number ("entrecno"), member record number ("memrecno"), and source code and member ID number ("srccode/memidnum"). All of the above fields are examples only. Other ways to configure a business operation are also possible. For example, if the user selects MemSearch, then a window may appear to allow the user to add/select desired data elements of the service model on which to search. The user may also choose to populate the flow with certain data elements drawn from the service model upon which the flow is based.

Figure 18:
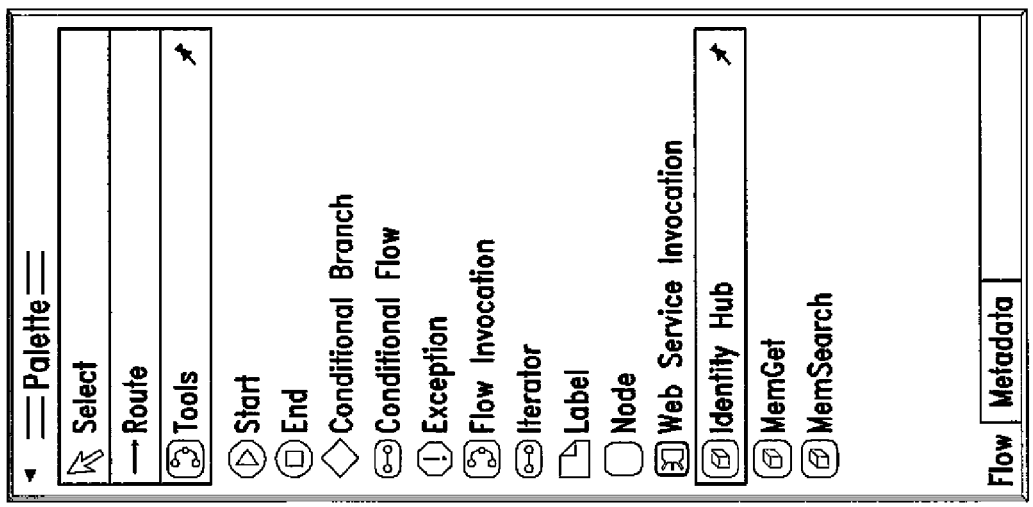
FIG. 18 is a screenshot depicting one example of one embodiment of a Flow Editor through which a user can create and customize flows.

FIG. 18 is a screenshot depicting one example of one embodiment of a Flow Editor through which several types of tools and objects are provided via a palette to a user for creating and customizing flows. In one embodiment, the palette includes two tabs or views through which the user can specify the logic to use when creating a particular flow. When selected, the "Metadata" tab shows the inputs, outputs, and temporary variables for use within a flow. Flow variables are temporary variables used in mappings within the flow. When selected, the "Flow" tab allows the user to graphically define and edit the flow logic. As described above, when the user creates a service operation, a corresponding file can be automatically created. The Flow Editor provides a graphical interface for editing flow data which can be saved in the file.

Using flows, a user can define rules for coordinating activities between Web Services, external data sources, MEI services, and the like. In the example of FIG. 18, the palette includes several pre-defined objects (e.g., icons) representing different flow elements (e.g., Start, End, Conditional Branch, Conditional Flow, Exception, Flow Invocation, Iterator, Label, Node, Web Service Invocation, etc.). As an example, to add a node, the user may simply click the node's icon in the palette (e.g., "Start") and click on an editor window (see FIG. 19). The user can then reposition the node or size is using a pointing device (e.g., a mouse). Other ways to implement the Flow Editor are also possible (e.g., drag-and-drop).

Start and End nodes indicate the beginning and end of flow logic. A Conditional Flow node provides a way to evaluate an expression to determine if nested flow logic is executed. It is similar to a Conditional Branch, but only allows for one testable expression which is configured on the conditional flow node itself. Exception creates a node whose purpose is to throw an exception. Flow Invocation invokes another flow within the same project and enables the flow logic to be reused for multiple top-level actions (e.g., enhanced composite views of data from various information sources). An iterator node provides a way to iterate through a collection of objects. Label provides a way to add comments to a flow (e.g., via a text box). Node provides an additional node for the flow and can be used to separate a route in order to organize many mappings, or it can be used to join multiple routes. Conditional Branch and Web Invocation will be described below with reference to FIGS. 19-20.

The palette also provides links to other functions of the Flow Editor. For example, "Select" provides a way for the user to select a particular route or node and "Route" provides a way for the user to link the various flow nodes together. In one embodiment, when a route is first added, it is displayed with a dashed line. Once a mapping has been created between the nodes, the line becomes solid. Other implementations are also possible. For example, a first color may be used to represent a route between nodes initially and a second color may be used to represent the route once the mapping is done.

Figure 19:
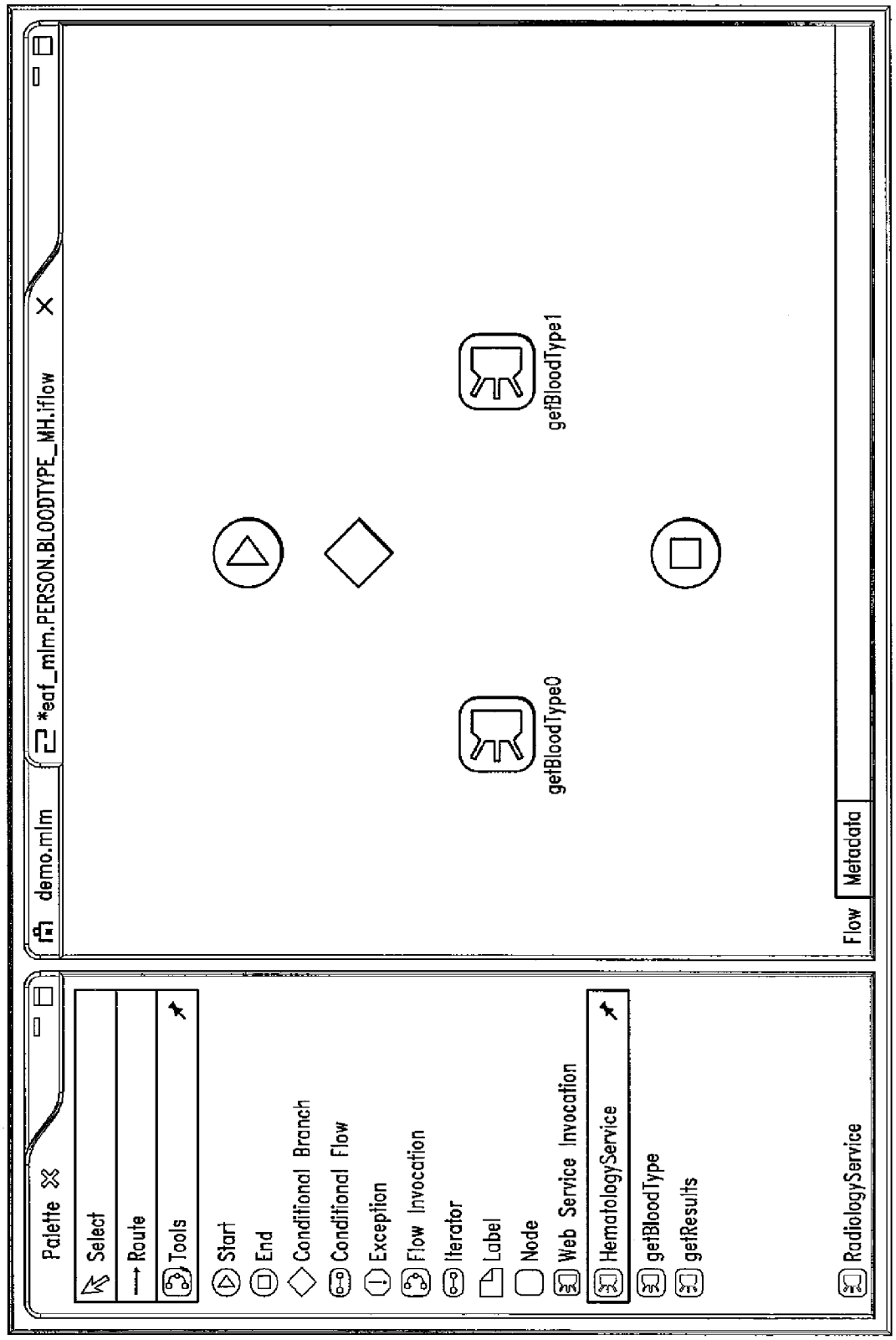
FIGS. 19 and 20 are screenshots depicting one example of how a flow can be created and customized by a user.
Figure 20:
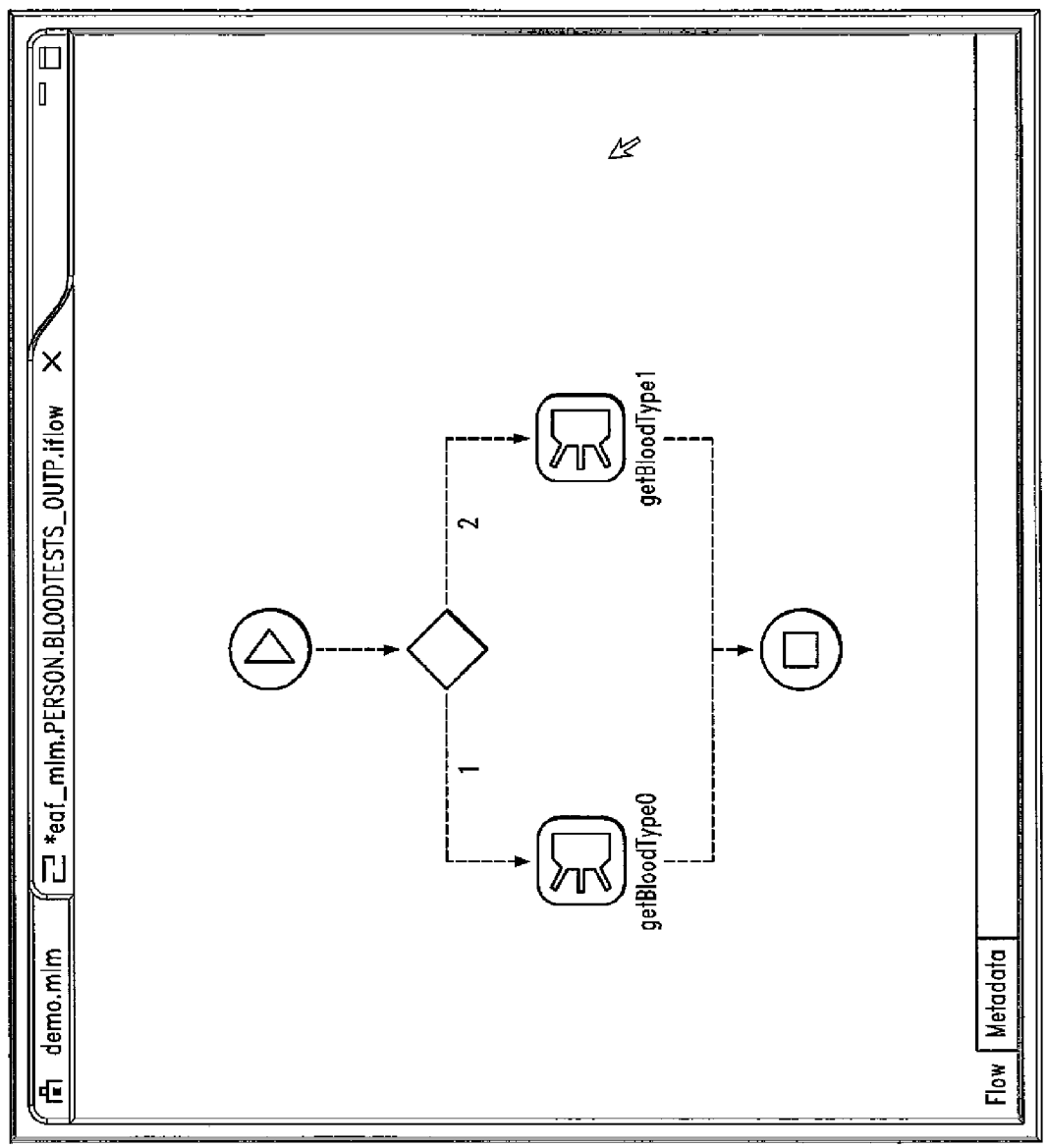

FIGS. 19 and 20 are screenshots depicting one example of how a flow can be created by a user. In this example, a Flow Editor displays two services, "HematologyService" and "RadiologyService." "HematologyService" has two operations, "getBloodType" and "getResults," according to a data model defined by the user. In defining the "getBloodType" operation, in this example, the user adds a conditional branch to indicate two possible routes. A conditional branch provides a way to evaluate an expression to determine which route to take to continue the execution of the flow. The user can define a specific expression for each branch of the node, and can specify the order in which the branches are evaluated, as well as the default branch. The branches of the node represent the potential routes that may be taken upon exiting the conditional branch. The expressions on these routes are evaluated to a Boolean value and can include simple rules based on the member data or any other data values available in the flow at that time.

In one embodiment, the Flow Editor may provide a "Properties" view or tab (not shown) in which values may be added for each of the properties of the conditional branch note (e.g., the default route, the branch execution order, the description to be displayed when a pointer is positioned over the conditional branch node, a label to the description, a unique identification for the conditional branch, location or coordinates of the conditional branch node as it exists in the Flow Editor, etc.). The properties of a route may differ based on the nodes that are routed together.

As exemplified by FIGS. 19 and 20, a route may simply be created by selecting Route in the tool palette, clicking on an edge or corner of the conditional branch node (shown in a diamond shape in FIG. 20) from which the route begins, and then clicking on a node where the route ends. These steps can be repeated for each route coming from the conditional branch node. In this case, there are two possible routes. If the route is specified as the conditional branch node default route, then the route does not need an expression. Otherwise, each route coming from a conditional branch node specifies a conditional expression that defines the execution logic for that branch.

The conditional expression can be any function that returns a Boolean value and can contain other nested functions as necessary. The following is an example of two conditional expressions:

equals(Customer.lastName, "Smith")
greaterThan(Customer.age, 30).

The completed flow may look like what is shown in FIG. 20. After the user has added flows for each action on each class in the Member Model of MEI 32, the user can assign mappings for each route in each flow. Mappings enable the user to assign inputs and outputs to each route thus created. The following examples illustrate some possible mapping expressions:

assign(Customer.firstName,
    WebService0.WebCustomer.firstName)
assign(30, WebService0.Customer.age)

One embodiment provides a set of pre-defined mapping functions. Thus, when a flow is created, a set of mappings can be automatically generated for the user. However, additional mappings may be needed. For example, a Web Service Invocation may be added to the flow shown in FIG. 19 to add an abstracted reference to a web service. In this case, a mapping function assigning inputs and outputs pertaining to the web service may need to be generated, imported, or otherwise incorporated. In one embodiment, routes with no mappings are displayed in broken lines. This may occur if the Member Model of MEI 32 or a back-end source is changed. Examples of how a user-define logical procedure (e.g., a business service operation flow defined by an operator according to a business service model) can invoke MEI services through mapping logic will now be described with reference to FIGS. 5-11.

Referring back to FIG. 5, for various reasons, such as regulatory laws or codes (e.g., the Health Insurance and Portability and Accountability Act or HIPAA), privacy concerns, concerns about storage space or efficiency, etc., it may not be desirable to store all the values of all the attributes or other information associated with a data record in data store 54 (e.g., in conjunction with a member data record). Thus, in addition to any identity information (e.g., attributes whose values are stored in data store 54 of MEI) comprised by a member type definition, in one embodiment, as discussed above, a member data record may be associated with a set of non-identity information (e.g., attributes whose values are stored externally to data store 54 of MEI). For example, the values for the non-identity attributes associated with a particular member data record may be stored at an information source 34, 36, 38 which stores the data record corresponding to that member data record and the values for the identity attributes of the member data record stored in the data record database (and which may also be stored at the information source 34, 36, 38 in conjunction with the data record corresponding to that member data record). By only storing identity information (e.g., values for identity attributes) for a member data record at MEI 32 the amount of data stored in data store 54 may be reduced and, by tailoring the identity information stored at data store 54 according to any pertinent laws, regulation, or desires of owners of information sources 34, 36, 38 these various laws, regulations, desires, etc. may be accounted for with regards to the storage of member data record data.

This arrangement, however, may present a number of difficulties. One of these difficulties is how to manage data stored in these disparate locations (e.g., in data store 54 and multiple information sources 34, 36, 38). Specifically, each of information sources 34, 36, 38 may not be managed by MEI 32 and may utilize any one of a number of formats, protocols, etc. Thus, to collect information corresponding to a member data record (e.g., both identity and non-identity information) on a particular member data record, attribute values associated with that member data record may need to be obtained from both data store 54 and from one or more information sources 34, 36, 38. It may be desirable, however, to present a unified view of a member record or entity to a user. In other words, to allow the gathering and storage of the various values of attributes associated with member data records to be transparent to a user of MEI.

To that end, attention is now directed to systems and methods for managing data stored in disparate locations. Embodiments of the present invention may allow attribute (or other) values associated with one or more member data records to be assembled and presented in a unified manner. More particularly, embodiments of the present invention may utilize a set of locally stored identity information associated with a member data record to determine a set of logical procedures corresponding to a set of externally stored non-identity information associated with the member data record. Each of this set of logical procedures may be operable to implement logic to retrieve values for one or more non-identity attributes from an information source.

Figure 5:
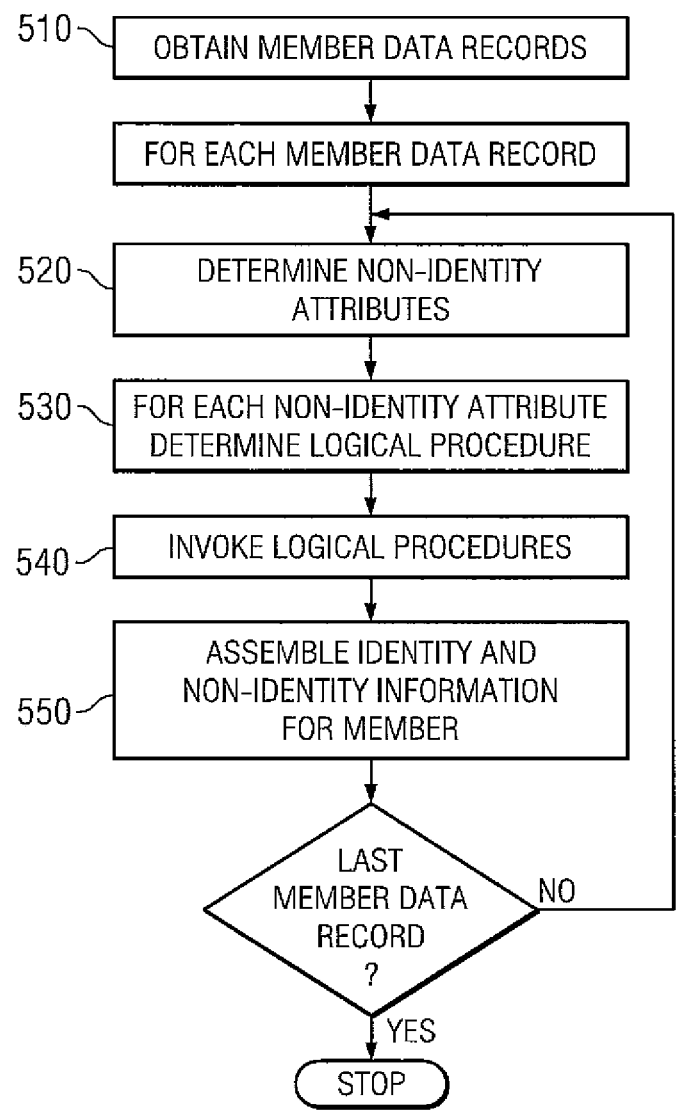
FIG. 5 is a flow diagram illustrating one embodiment of a method for managing data stored externally.

Turning to FIG. 5 a flow diagram of one embodiment of a method for managing data stored externally (e.g., in information sources) in conjunction with data stored locally (e.g., in data store 54 of MEI) is depicted. At step 510 MEI may generate or otherwise obtain a set of member data records. These member data records may be generated in response to a query received from an operator 40, 42, 44 as will be discussed later. Each of these members data record may comprise the set of identity information (e.g., values for identity attributes) associated with that member data record (e.g., stored in data store 54). Based on the member type definition to which the member data record corresponds a set of attributes whose values are non-identity information (e.g., not stored in data store 54) may be determined at step 520. For each of these non-identity attributes of these member data records, a logical procedure may be determined at step 530 to obtain values for the non-identity attributes for each of the members, if it exists, and these logical procedures invoked at step 540. A logical procedure may have a defined set of inputs and outputs (for example, based on the attribute type and an associated member type definition) and comprise logic operable to retrieve the value for a particular non-identity attribute from an information source. This retrieval may entail communication with a particular information source according to the protocol or format utilized by that information source, or may entail the invocation of a web service provided by that information source, or almost any other type of communication. For each of the member data records then, the values of the non-identity attributes obtained by each of the logic flows invoked at step 540 may be assembled with the identity information stored locally in data store 54 according to the member type definition or other format at step 550.

Figure 6:
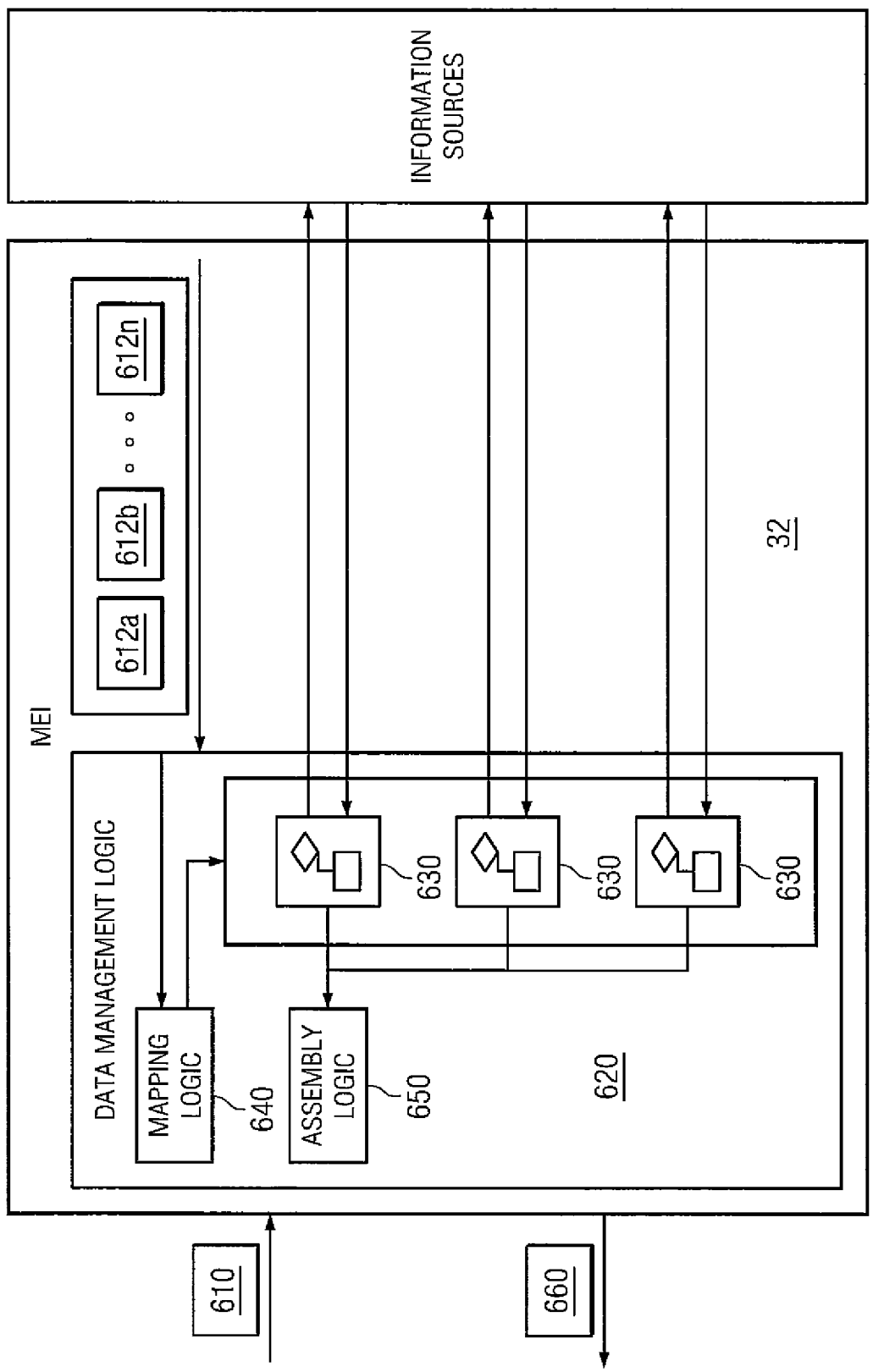
FIG. 6 depicts an example of one embodiment of managing data stored in disparate locations in conjunction with responding to a query from a user.

The embodiment of the methodology depicted in FIG. 5 may be better explained with reference to FIG. 6 which depicts an example of one embodiment of managing data stored in disparate locations in conjunction with responding to a query from a user. MEI 32 may receive query 610 from a user. Query 610 may comprise a set of criteria provided by the user and a set of desired results which may comprise a set of attributes, member data records, or entities. For example, a request may comprise a name (e.g., such as "John") and the desired results may comprise the attributes of address and a social security number. As noted above, request 610 may be formed according to an API provided by MEI 32. Based on this query 610, MEI 32 may obtain a set of member data records 612a ... n utilizing the set of criteria in query 610 and provide these member data records 612 to data management logic 620. Each of member data records 612 may be of a particular member data type and comprise identity information for the member data record which may include an associated information source for the member data record 612. Using an attribute map corresponding to the member data type mapping logic 640 may reference a set of logical procedures 630, where each of the set of logical procedure 630 may be operable to retrieve a value for a non-identity attribute associated with the member data record from an information source. More particularly, in one embodiment, each of logical procedures 630 may be invoked with at least a portion of the identity information associated with the member data record 612 and may utilize this identity information to access an information source to retrieve values for the non-identity attribute associated with the logical procedure 630.

Using the identity information associated with the member data record 612 and the attribute values retrieved by each of logical procedures 630, assembly logic 650 may assemble a result to return to the initiator of query 610. This result may be assembled according to an API provided by MEI 32, or another format, and may correspond to the API with which query 610 was initiated. In one particular embodiment, the format of the assembled result may correspond to the member type definition for the member data record. Result 660 assembled by assembly logic 650 may then be returned to the initiator of query 610.

It may be helpful here to reference a particular example. For purposes of this example, therefore, assume that MEI 32 has a member type definition for a person which comprises four attributes, a "Name" attribute, an "Address" attribute, a "Social Security No." attribute and an "Invoice No." attribute. The identity information corresponding to this member type definition is a value for the "Name" attribute. Now suppose that query 610 comprises a particular phone number as a criterion and based upon this criterion MEI 32 locates two member objects 612a and 612b. Member object 612a is associated with information source 34 while member object 612b is associated with information source 36.

Figure 7:
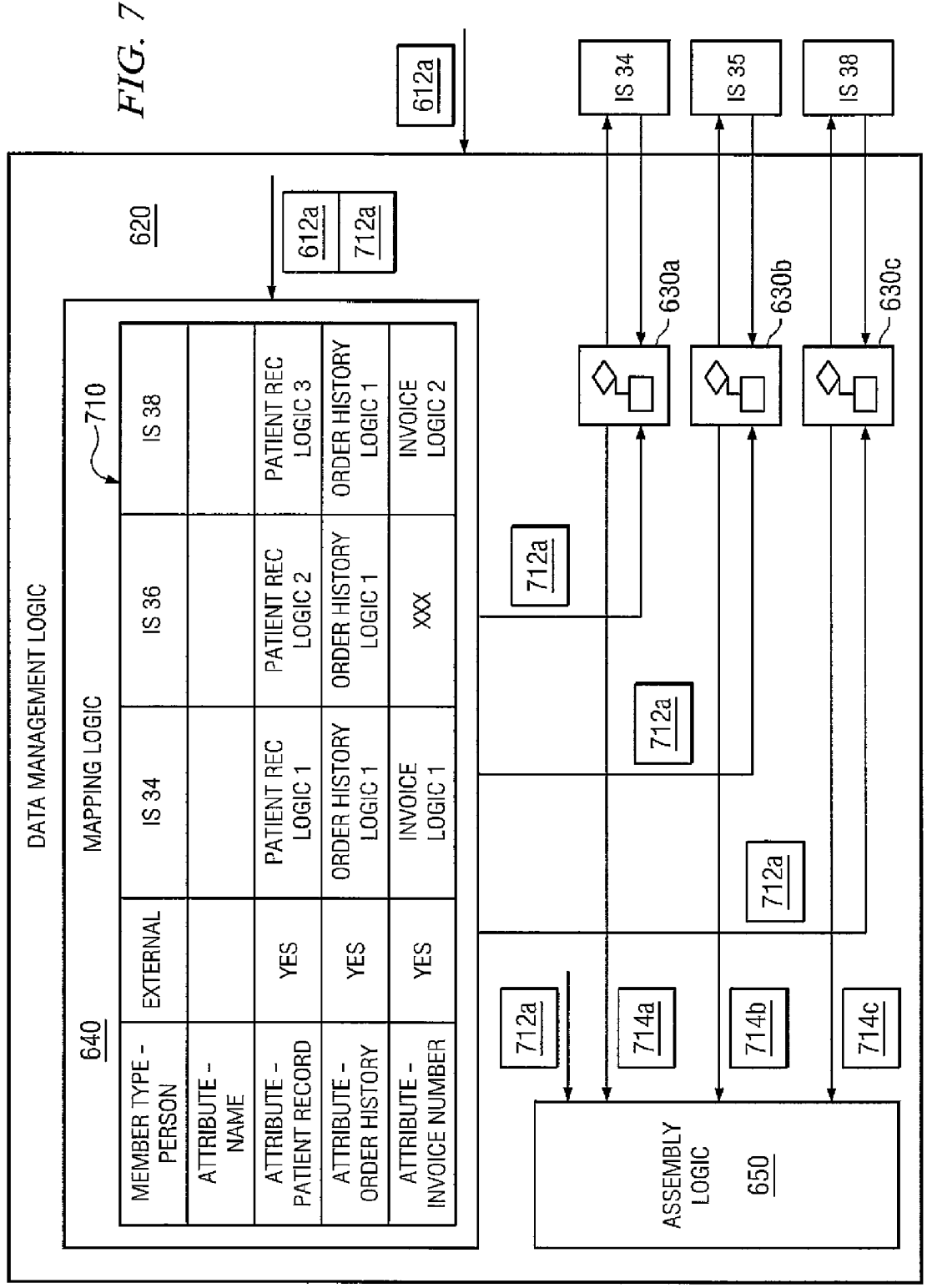
FIGS. 7 and 8 are block diagrams illustrating embodiments of processing of member data records.
Figure 8:
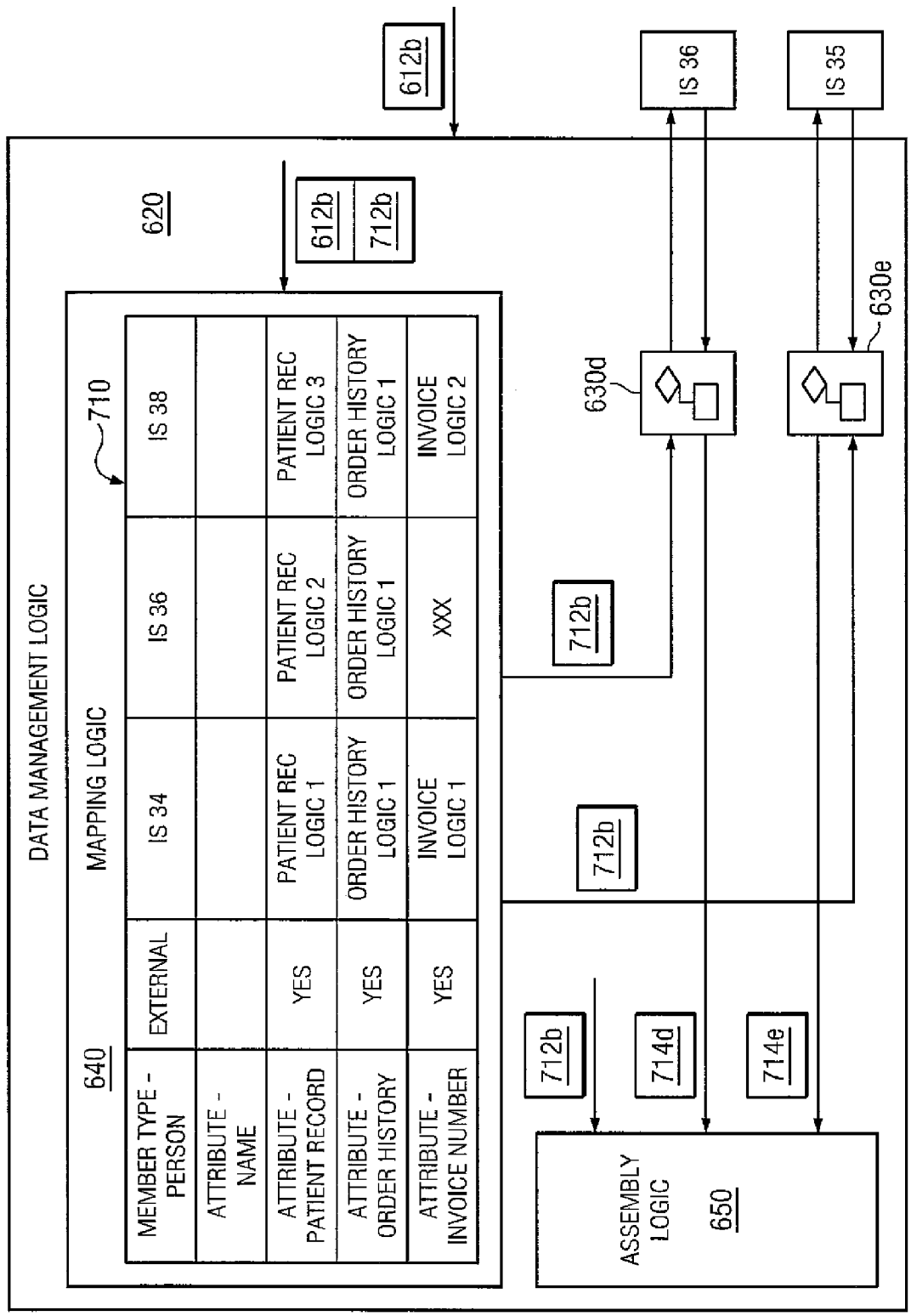

FIGS. 7 and 8 depict the processing of member data records 612a and 612b respectively. Referring first to FIG. 7, a block diagram of one embodiment of the processing of member data record 612a of the current example is depicted. Member data record 612a may be provided to data management logic 620 (e.g., including the identity information 712a associated with member data record 612a) which in this case may comprise a value for the "Name" attribute associated with member data record 612a. Mapping logic 640 may then utilize table 710 to determine a set of logical procedures 630 to obtain values for the non-identity attributes (e.g., external to MEI) of member data record 612a. In the example depicted, as member data record 612a is associated with information source 34, mapping logic 640 may determine that the "Name" attribute is not a non-identity attribute and therefore no logical procedure needs to be determined for this attribute. Mapping logic 640 may also determine, based on the information source associated with member data record 712a (e.g., IS 34), that the "Address Logic 1" procedure should be invoked to obtain the value for the "Address" attribute of member data record 612a, that the "SS Logic 1" procedure should be invoked to obtain the value for the "Social Security No." attribute of member data record 612a and that the "Invoice Logic 1" procedure should be invoked to obtain the value for the "Invoice No." attribute of member data record 612a.

Each of those logical procedures 630 may then be invoked and provided with the identity information 712a (e.g., the value of the "Name" attribute) associated with member data record 612a. In this example, logical procedure 630a may be "Address Logic 1" operable to obtain the value 714a of the "Address" attribute associated with member data record 612a from information source 34, logical procedure 630b may be "SS Logic 1" operable to obtain the value 714b for the "Social Security No." attribute associated with member data record 612a from information source 34 and logical procedure 630c may be "Invoice Logic 1" operable to obtain the value 714c for the "Invoice No." attribute associated with member data record 612a from information source 34.

The identity information 712a associated with member data record 612a can then be provided to assembly logic 650 along with each of the values 714 for the attributes obtained by logical procedures 630a, 630b, 630c (e.g., non-identity information). The identity information 712a and non-identity information corresponding to member data record 612a may then be formatted or otherwise processed (e.g., according one or more logical procedures as explained in more detail below) by assembly logic 650 and returned to the operator 40, 42, 44 which initiated a query.

Moving now to FIG. 8, a block diagram of one embodiment of the processing of member data record 612b of the current example is depicted. Member data record 612b may be provided to data management logic 620 (e.g., including the identity information 712b associated with member data record 612b) which in this case may comprise a value for the "Name" attribute associated with member data object 712b. Mapping logic 640 may then utilize table 710 to determine a set of logical procedures 630 to obtain values for the non-identity attributes (e.g., external to MEI) of member data record 612b. In the example depicted, as member data record 612b is associated with information source 36, mapping logic 640 may determine that the "Name" attribute is not a non-identity attribute and therefore no procedure needs to be determined for this attribute. Mapping logic 640 will also determine based on the information source associated with member data record 612b (e.g., IS 36) that the "Address Logic 2" procedure should be invoked to obtain the value for the "Address" attribute of member data record 612b, that the "SS Logic 1" procedure should be invoked to obtain the value for the "Social Security No." attribute of member data record 612b and that no logical procedure should be invoked to obtain the value for the "Invoice No." attribute of member data record 612b (e.g., because no value for "Invoice No." may be stored for data records of information source 36).

Each of those logical procedures 630 may then be invoked and provided with the identity information 712b (e.g., the value of the name attribute) associated with member data record 612b. In this example, logical procedure 630d may be "Address Logic 2" operable to obtain the value 714d of the "Address" attribute associated with member data record 612b from information source 36 and logical procedure 630e may be "SS Logic 1" operable to obtain the value 714e for the "Social Security No." attribute associated with member data record 612b from information source 36.

The identity information 712b associated with member data record 612b can then be provided to assembly logic 650 along with each of the values 714 for the attributes obtained by logical procedures 630d, 630e (e.g., non-identity information). The identity information 712b and non-identity information corresponding to member data record 612b may then be processed by assembly logic 650 to form a result and the result returned to the user which initiated the query.

A few things will be noted after a review of the above example. First, it will be observed that one logical procedure may be associated with the retrieval of a value of an attribute of a member data record from multiple information sources or individual logical procedures for the retrieval of the value of an attribute may be defined for individual data sources, or any combination thereof. In other words, logical procedures may be tailored or otherwise operable to interact with one or more of the information sources to obtain a value according to almost any type of communication protocol, storage format, etc utilized by an information source or otherwise desired. Furthermore, each of logical procedures may accomplish almost any type of processing on these values, such as parsing of the obtained values, etc.

The definition of these various logical procedures may also occur in almost any manner desired. In one embodiment, for example, a user may utilize a graphical interface to define each of the logical procedures where the graphical interface may offer a set of visual representations of functionality which the user may assemble and a logical procedure instantiated from the graphical representation created by the user. These logical procedures may also be hard coded during installation or configuration of MEI, the logical procedures may be provided by one or more third party vendors, etc.

Using embodiments of the present invention a variety of other functionality may also be implemented in managing data stored in disparate locations. For example, data management logic 620 may receive a user identification along with the set of member data object and based upon this user identification apply a set of permissions to the identity attributes and non-identity attributes to determine if the user represented by the user identification has permission to receive values for these attributes such that assembly logic 650 may assemble a reply to a query based on these permissions. A wide variety of these security protocols may similarly be implemented, such that only values of certain attributes associated with member data records may be accessed.

Embodiments of the present invention may also be utilized to determine which values of attributes are to be returned in response to a query from a user. In many cases, a member data record which is to be returned in response to a user request, or an entity to be returned to a user in response to a query (which may be comprised of multiple member data records) may have multiple values associated with one or more of the attributes associated with the member data record or the entity. For example, a member data record may have two or more values corresponding to a name attribute, where one value is the current value of the name attribute for the member data record and another value for the name attribute may be a historical value for the name attribute. Similarly, an entity may comprise two or more linked member data records where one of the member data records of the entity may have one value for a name attribute and another member data record associated with the entity may have a different value for the name attribute. If each of these values for a member data record or entity is returned to a user in response to a query it may require a great deal of review for a user to locate the values or information that he desires. Thus, it would be desirable if the values of attributes associated with member data records and entities could be refined or composited according to a user's desires before being returned to a user.

To address this desire, among others, attention is now directed to systems and methods for refining or compositing one or more member data records. More particularly, embodiments of the present invention may apply a logical procedure to the values of attributes corresponding to one or more data records to select one or more values of one or more attributes. Specifically, embodiments of the invention may apply a logical procedure referenced in a user query to composite member data records obtained as a result of the query, such that the response to the query comprises the values for attributes as determined by the application of the logical procedure. A variety of these logical procedures may be defined such that a user may easily obtain desired results through the selection of one or more of these logical procedures.

Figure 9:
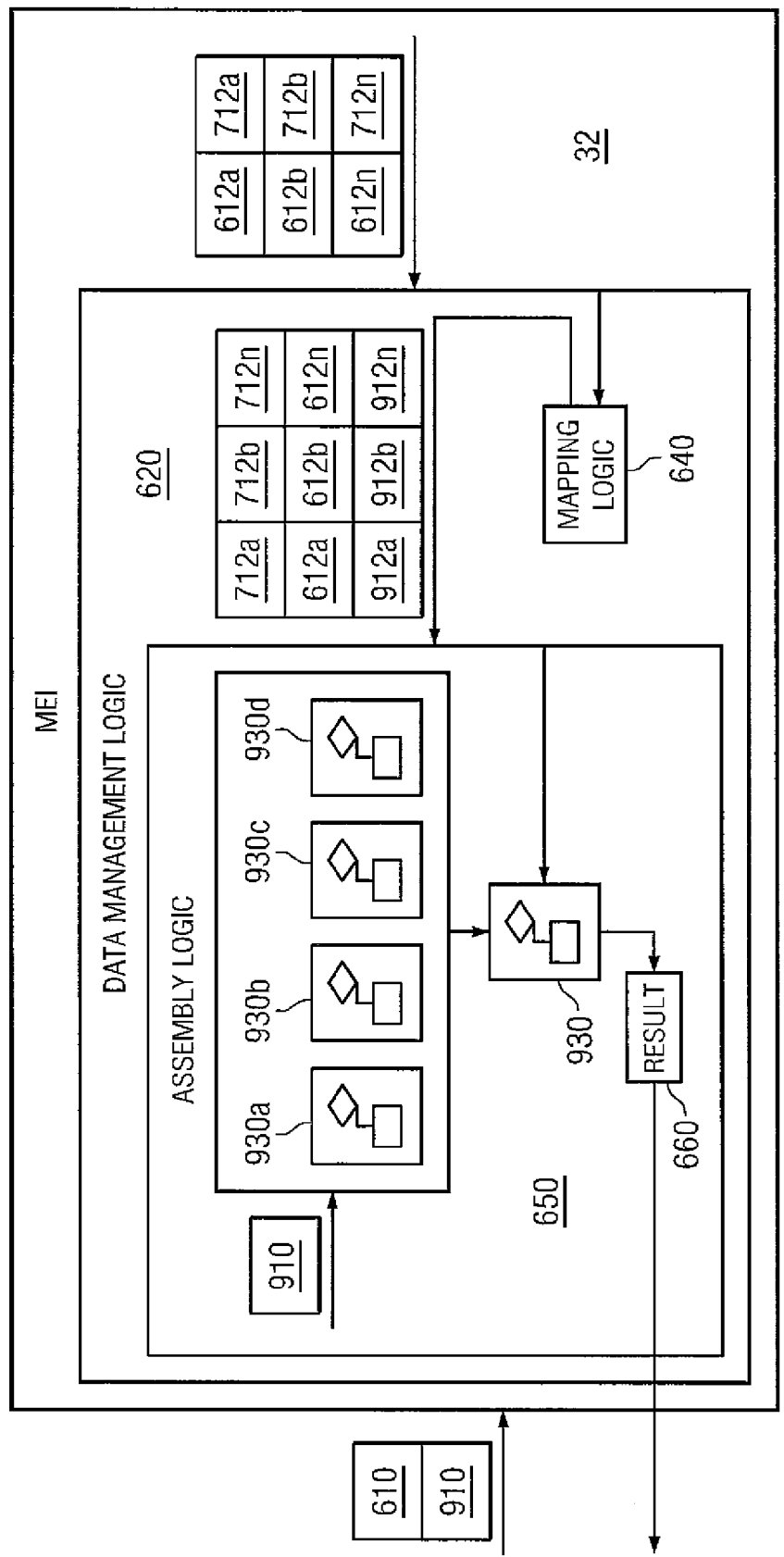
FIG. 9 depicts one embodiment of utilizing a logical procedure for compositing member data records.

Embodiments of the systems and methods of the present invention may be better understood with reference to FIG. 9 which depicts one embodiment of utilizing a logical procedure for the compositing of member data records. As discussed above, in response to a query 610 from a user, data management logic 620 may receive member data records 612a, b ... n and associated values 712a b ... n for identity attributes of the member data record 612. Values 912a b ... n for non-identity attributes of member data records 612 may be obtained using logical procedures selected by mapping logic 640 (as discussed above). Thus, a set of member data records 612a comprising values 712 for the identity attributes of the member data record 612a and values 912 for non-identity attributes may be provided to assembly logic 650 such that assembly logic 650 may assemble result 660 to return to the user in response to query 610.

In one embodiment, query 610 from a user may comprise a reference 910 to a logical procedure 930 which is to be applied to member data records 612a and their associated attribute values 712, 912 to generate result 660 to be returned in response to query 610. Each of logical procedures 930a ... d may be operable to process one or more member data records 612 either alone or in conjunction with one another according to a defined set of logical steps to select values and attributes to be returned to a user in result 660. For example, a logical procedure 930 may select values for attributes of a member data record to return to a user, a logical procedure 930 may process one or more member records of an entity to select values for attributes of the entity to return to a user, or both (selecting attributes of one or more member data records related as an entity and then further processing the values of the attributes selected for each of the related member data records to select values for attributes of the entity to return to the user). Put another way, a logical procedure may refine the set of, or composite the values of, attributes for one or more member data records to select a final set of values for one or more attributes such that these final values may be returned to the user in result 660. By allowing a user to select a logical procedure 930 for the compositing of the values of attributes of member data records a user may be presented with values or attributes that more closely match a users desires.

Figure 10:
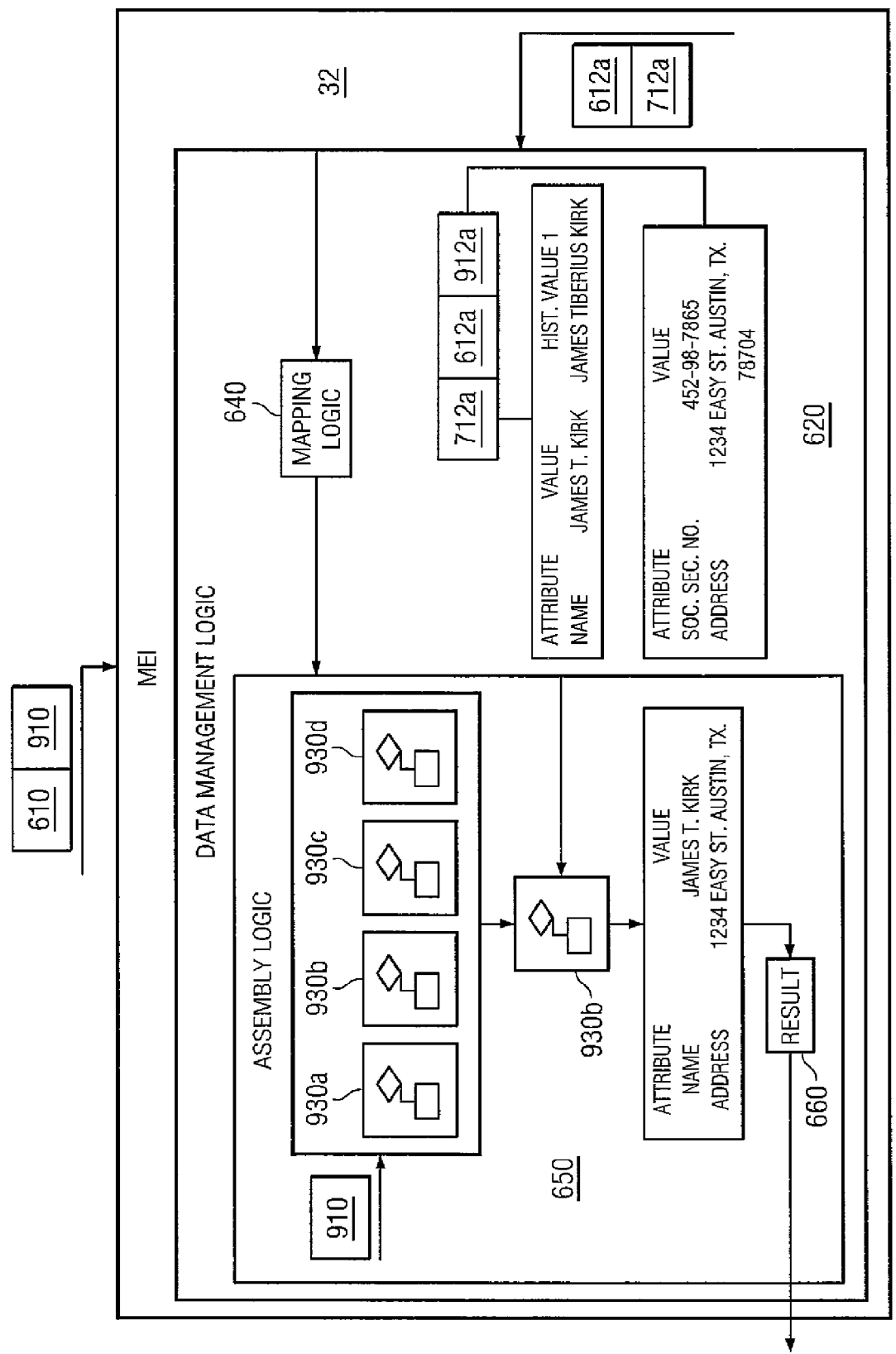
FIGS. 10 and 11 depict embodiments of processing of example member data records.
Figure 11:
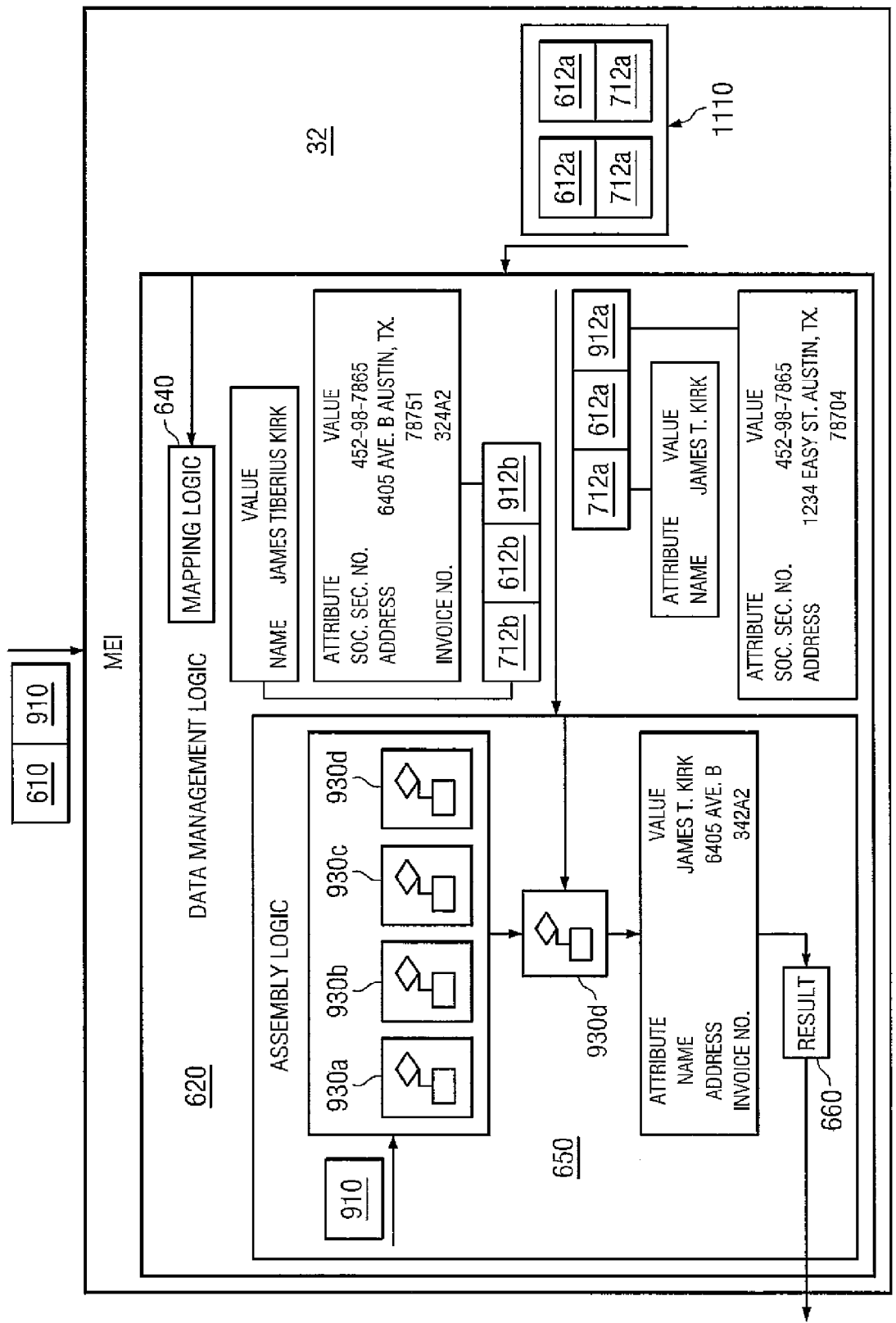

It may be helpful here to illustrate examples of the processing of member data records using a logical procedure. FIGS. 10 and 11 depict examples of this processing. In particular, FIG. 10 depicts one embodiment of the processing of an example member data record to select values for attributes of the member data record while FIG. 11 depicts the processing of example member data records of an entity to composite values for desired attributes corresponding to the entity.

Turning first to FIG. 10, one embodiment of the processing of an example member data record 612a is depicted. Suppose for purposes of this example a user has submitted query 610 to MEI 32 and that member data record 612a has been provided to data management logic 620 such that it can be processed to compose response 660 to the user. Now suppose that member data record 612a is associated with values 712a for the identity attribute of "Name" and that values 712a for the "Name" attribute comprises a current value of "James T. Kirk" and a first historical value of "James Tiberius Kirk". Further suppose that member data record 612a is associated with values 912a for the non-identity attributes of "Social Security No." and "Address" and that value 912a for the "Social Security No." is "452-98-7865" and the value 912a for "Address" is "1234 Easy St., Austin, Tx. 78704".

The user who initiated query 610 may, however, not wish to view values for every attribute of the member data records returned to him, or all the values of an attribute. Consequently, in query 610 a user may select or specify a logical procedure 930a . . . d such that the member data records responsive to query 610 may be processed according to the logical procedure 930 selected to composite or refine the set of attributes or values for those attributes returned to the user such that the user can view desired results to his query.

Continuing with the example above, the user may desire to view only the most recent value for the "Name" attribute and the value for the "Address" attribute. The user may also with to only view the street address, city and state information for the "Address" attribute (e.g., not any zip code information). In order to be presented with his desired results then, in query 610 the user may submit reference 910 to logical procedure 930b. Logical procedure 930b may be operable to select the most recent value for the "Name" attribute of a member data record, and the street address, city and state information for the "Address" attribute. With respect to this example, when member data record 612a is processed using logical procedure 930b referenced in query 910, the value "James T. Kirk" is selected for the "Name" attribute the value "11234 Easy St., Austin, Tx. 78704" is selected for the "Address" attribute and is further processed such that the value for the "Address" attribute becomes "1234 Easy St., Austin, Tx.". The set of values for selected attributes produced by logical procedure 930b (in this case the attributes of "Name" and "Address" and their respective values of "James T. Kirk" and "1234 Easy St., Austin, Tx.") may then be used in assembling result 660 to send to the user in response to query 610.

Proceeding to FIG. 11 one embodiment of the processing of example member data records 612a and 612b which comprise an entity 1110 is depicted. Suppose for purposes of this example a user has submitted query 610 to MEI 32 and that member data records 612a and 612b which are linked (as described above) as an entity 1110 have been provided to data management logic 620 such that member data records 612a and 612b can processed to compose response 660 to the user regarding entity 1110. Now suppose that member data record 612a is from information source 34 and is associated with values 712a for the identity attribute of "Name" and that values 712a for the "Name" identity attribute further comprises a value of "James T. Kirk". Further assume that member data record 612a is associated with values 912a for the non-identity attributes of "Social Security No." and "Address" and that the value 912a for the "Social Security No." is "452-98-7865" and the value 912a for "Address" is "1234 Easy St., Austin, Tx. 78704". Additionally suppose that member data record 612b is from information source 36 and is associated with values 712b for the identity attribute of "Name" and that values 712b for the "Name" identity attribute further comprises a value of "James Tiberius Kirk". Further suppose that member data record 612b is associated with values 912b for the non-identity attributes of "Social Security No.", "Invoice No." and "Address" and that value 912b for the "Social Security No." is "452-98-7865", the value 912b for "Invoice No." is "324A2" and the value for "Address" is "6405 Ave. B, Austin, Tx. 78751".

The user who initiated query 610 may, however, not wish to view values for every attribute of an entity (e.g., multiple linked member data records) returned to him, or all the values of an attribute. Consequently, in query 610 a user may select or specify a logical procedure 930a . . . d such that the member data records responsive to query 610 may be processed according to the logical procedure 930 selected to composite or refine the set of attributes or values for those attributes returned to the user and the user can view the desired results to his query.

Continuing with the example above, in order to be presented with his desired results then, in query 610 the user may submit reference 910 to logical procedure 930d. Logical procedure 930d may be operable to select the value for the "Name" attribute associated with a member data record from information source 34 if it exists, the value for the "Address" attribute associated with a member data record from information source 36 if it exists, the value for an "Invoice No." attribute. Logical procedure 930d may be further operable to process the selected value for the "Address" attribute to obtain the street information from the "Address" attribute. With respect to this example, when member data records 612a and 612b are processed using logical procedure 930d referenced in query 610, the value "James T. Kirk" is selected for the "Name" attribute the value "6405 Ave. B Austin, Tx 78751" is selected for the "Address" attribute and is further processed such that the value for the "Address" attribute becomes "6405 Ave. B", and the value "324A2" is selected for the "Invoice No." attribute. The set of values for selected attributes produced by logical procedure 930d (in this case the attributes of "Name", "Invoice No." and "Address" and their respective values of "James T. Kirk", "324A2" and "6405 Ave. B") may then be used in assembling result 660 to send to the user in response to query 610.

Again, after reviewing the above descriptions and examples it will be realized that these logical procedures may refine and composite or otherwise process the value of attributes of one or more member data records according to almost any logic desired. The definition of these various logical procedures may also occur in almost any manner desired. In one embodiment, for example, a user may utilize a graphical interface to define each of the logical procedures where the graphical interface may offer a set of visual representations of functionality which the user may assemble to define a desired logical procedure and a logical procedure instantiated from the graphical representation created by the user. These logical procedures may also be hard coded during installation or configuration of MEI such that a user may select from a set of pre-define logical procedures, the logical procedures may be provided by one or more third party vendors, etc.

In the foregoing specification, the invention has been described with reference to specific embodiments. However, it should be understood that the description is by way of example only and is not to be construed in a limiting sense. It is to be further understood, therefore, that numerous changes in the details of the embodiments of this invention and additional embodiments of this invention will be apparent to, and may be made by, persons of ordinary skill in the art having reference to this description. It is contemplated that all such changes and additional embodiments are within the scope of the invention as detailed in the following claims.

What is claimed is:

1. A system comprising:
    a processor; and
    one or more computer readable storage media accessible by the processor and storing computer instructions executable by the processor to implement an interface layer between one or more users and a master entity index (MEI) system employing a first data model, the interface layer receiving a query for the MEI system and interacting with the MEI system based on the query to provide desired information, the interface layer comprising a set of interfaces and business services, wherein each of the business services is defined according to a second different custom data model created by the one or more users with elements mapped to elements of the first data model, is associated with one of the interfaces, and comprises one or more operations, wherein each of the one or more operations is associated with a logical procedure that when executed interacts with the MEI system based on the query and in accordance with the first data model and provides the desired information according to the second data model from information from the MEI system in the first data model;
    wherein the logical procedure is defined by the one or more users via a set of graphical objects on a graphical interface representing functional operations for the logical procedure, and wherein the graphical interface enables the one or more users to select and arrange the graphical objects to graphically define operational logic flow of the logical procedure for providing the desired information according to the second data model;
    wherein the logical procedure invokes a service function of the MEI system to obtain outputs defined for a particular operation by the one or more users.

2. The system of claim 1, wherein the logical procedure is mapped to a service function provided by the MEI system, to a different business service operation, or to another logical procedure.

3. The system of claim 1, wherein the set of interfaces allows queries from the one or more users to be submitted utilizing Simple Object Access Protocol (SOAP).

4. The system of claim 1, wherein a graphical representation of the logical procedure includes at least two nodes and one route connecting the at least two nodes.

5. The system of claim 1, wherein the logical procedure is persisted as an XML file.

6. The system of claim 1, wherein the logical procedure interacts with the MEI system via an application programming interface (API) provided by the MEI system.

7. A computer readable memory device including a non-transitory storage medium carrying computer instructions executable by a processor to implement an interface layer between one or more users and a master entity index (MEI) system employing a first data model, the interface layer receiving a query for the MEI system and interacting with the MEI system based on the query to provide desired information, the interface layer comprising a set of interfaces and business services, wherein each of the business services is defined according to a second different custom data model created by the one or more users with elements mapped to elements of the first data model, is associated with one of the interfaces, and comprises one or more operations, wherein each of the one or more operations is associated with a logical procedure that when executed interacts with the MEI system based on the query and in accordance with the first data model and provides the desired information according to the second data model from information from the MEI system in the first data model;
    wherein the logical procedure is defined by the one or more users via a set of graphical objects on a graphical interface representing functional operations for the logical procedure, and wherein the graphical interface enables the one or more users to select and arrange the graphical objects to graphically define operational logic flow of the logical procedure for providing the desired information according to the second data model;
    wherein the logical procedure invokes a service function of the MEI system to obtain outputs defined for a particular operation by the one or more users.

8. The computer readable memory device of claim 7, wherein the logical procedure is mapped to a service function provided by the MEI system, to a different business service operation, or to another logical procedure.

9. The computer readable memory device of claim 7, wherein the set of interfaces allows queries from the one or more users to be submitted utilizing Simple Object Access Protocol (SOAP).

10. The computer readable memory device of claim 7, wherein a graphical representation of the logical procedure includes at least two nodes and one route connecting the at least two nodes.

11. The computer readable memory device of claim 7, wherein the logical procedure is persisted as an XML file.

12. A method for service provisioning, comprising:
    enabling a user to define, via a graphical interface, business service operations according to a custom business service model created by the user, wherein inputs and outputs to each of the business service operations are defined in the business service model, wherein the business service operations reside within an interface layer implemented between one or more users and a master entity index (MEI) system employing a data model different than the business service model with elements mapped to elements of the business service model, and wherein the interface layer receives a query for the MEI system and interacts with the MEI system based on the query to provide desired information;
    enabling the user to define and edit a logical procedure for each of the business service operations that when executed interacts with the MEI system based on the query and in accordance with the different data model and provides the desired information according to the business service model from information from the MEI system in the different data model, wherein the logical procedure is defined by the one or more users via a set of graphical objects on the graphical interface representing functional operations for the logical procedure, and wherein the graphical interface enables the one or more users to select and arrange the graphical objects to graphically define operational logic flow of the logical procedure for providing the desired information according to the business service model;

mapping the logical procedure to a service function provided by the master entity index (MEI) system; and invoking the service function to obtain the outputs for the business service operations.

13. The method of claim 12, further comprising returning the outputs to the user via the graphical interface.

14. The method of claim 12, further comprising enabling the user to assign the mapping via the graphical interface.

15. The method of claim 12, further comprising automatically creating a flow file corresponding to each of the business service operations.

16. The method of claim 12, further comprising automatically providing one or more predefined mapping functions for each of the business service operations.

* * * * *